(12) United States Patent
Miller et al.

(10) Patent No.: US 11,124,490 B2
(45) Date of Patent: Sep. 21, 2021

(54) AUTOTAXIN INHIBITORS

(71) Applicants: UNIVERSITY OF TENNESSEE RESEARCH FOUNDATION, Memphis, TN (US); UNIVERSITY OF MEMPHIS, Memphis, TN (US)

(72) Inventors: Duane D. Miller, Memphis, TN (US); Gabor G. Tigyi, Memphis, TN (US); Souvik Banerjee, Memphis, TN (US); Abby L. Parrill-Baker, Memphis, TN (US)

(73) Assignees: UNIVERSITY OF TENNESSEE RESEARCH FOUNDATION, Memphis, TN (US); UNIVERSITY OF MEMPHIS, Memphis, TN (US)

( * ) Notice: Subject to any disclaimer, the term of this patent is extended or adjusted under 35 U.S.C. 154(b) by 288 days.

(21) Appl. No.: 16/305,345

(22) PCT Filed: Jun. 2, 2017

(86) PCT No.: PCT/US2017/035629
§ 371 (c)(1),
(2) Date: Nov. 28, 2018

(87) PCT Pub. No.: WO2017/210527
PCT Pub. Date: Dec. 7, 2017

(65) Prior Publication Data
US 2020/0317626 A1    Oct. 8, 2020

Related U.S. Application Data

(60) Provisional application No. 62/345,472, filed on Jun. 3, 2016.

(51) Int. Cl.
*C07D 295/26* (2006.01)
*C07D 265/30* (2006.01)
*C07D 241/04* (2006.01)

(52) U.S. Cl.
CPC ......... *C07D 265/30* (2013.01); *C07D 241/04* (2013.01); *C07D 295/26* (2013.01)

(58) Field of Classification Search
CPC .................................................. C07D 295/26
See application file for complete search history.

(56) References Cited

U.S. PATENT DOCUMENTS

2005/0113450 A1 * 5/2005 Thorarensen ........... A61P 31/02
514/562
2009/0163545 A1    6/2009 Goldfarb

FOREIGN PATENT DOCUMENTS

| WO | 2008/071398 A1 | 6/2008 | |
|---|---|---|---|
| WO | 2014/040077 A1 | 3/2014 | |
| WO | WO-2014106019 A2 * | 7/2014 | ............ A61K 31/55 |
| WO | 2014/145642 A2 | 9/2014 | |

OTHER PUBLICATIONS

Chemical Abstracts Registry No. 91619-83-9, indexed in the Registry file on STN CAS ONLINE Nov. 16, 1984. (Year: 1984).*
Chemical Abstracts Registry No. 1386791-69-0, indexed in the Registry file on STN CAS ONLINE Aug. 6, 2012. (Year: 2012).*
Chemical Abstracts Registry No. 380434-67-3, indexed in the Registry file on STN CAS ONLINE Jan. 4, 2002. (Year: 2002).*
PubChem CID 2334818, National Center for Biotechnology Information. PubChem Compound Summary for CID 2334818. https://pubchem.ncbi.nlm.nih.gov/compound/2334818. Accessed Feb. 9, 2021, create date Jul. 15, 2005. (Year: 2005).*
Benesch et al. (2014) Inhibition of autotaxin delays breast tumor growth and lung metastasis in mice. The FASEB Journal, vol. 28, No. 6, pp. 2655-2666.
Database REGISTRY [online] RN 1387977-14-1, Aug. 8, 2012, Retrieved from STN.
Database REGISTRY [online] RN 1043289-70-8, Aug. 24, 2008, Retrieved from STN.

* cited by examiner

*Primary Examiner* — Laura L Stockton
(74) *Attorney, Agent, or Firm* — Lathrop GPM LLP; Brian C. Trinque

(57) ABSTRACT

The present disclosure provides novel ATX inhibitors, and pharmaceutical compositions comprising said inhibitors, as well as methods of treatment comprising administration of said inhibitors.

1 Claim, 13 Drawing Sheets

FIGURE 1

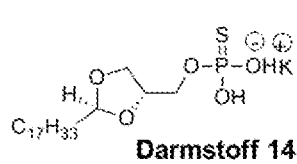

Darmstoff 14
The University of Tennessee
$IC_{50}$ = 252 nM
Molecular Weight = 474.19
logp = -4.2

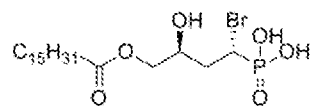

anti-Bromophosphonate-LPA
The University of Utah Research Foundation
$IC_{50}$ = 22 nM
Molecular Weight = 486.17
logp = 5.38

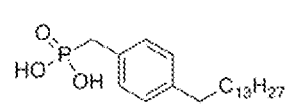

RG-3-339
The University of Tennessee
$IC_{50}$ = 252 nM
Molecular Weight = 368.49
logp = 6.5

Lipid-like ATX inhibitors

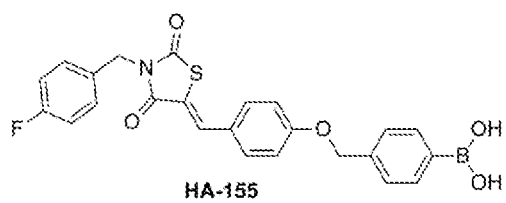

HA-155
Netherlands Cancer Institute
$IC_{50}$ = 5.7 nM
Molecular Weight = 463.28
logp = 2.7

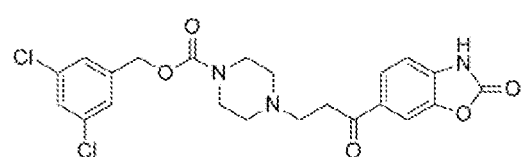

PF-8380
Pfizer
$IC_{50}$ = 2.8 nM
Molecular Weight = 478.32
logp = 2.6

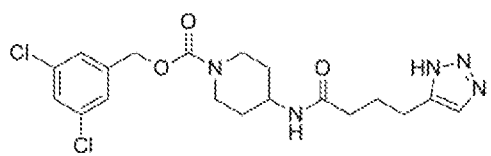

Novartis 2014
$IC_{50}$ = 2 nM
Molecular Weight = 440.32
logp = 2.5

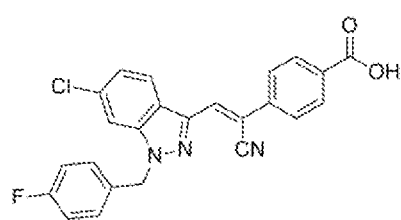

PharmAkea 2015
$IC_{50}$ = 500 nM
Molecular Weight = 431.84
logp = 3.7

Non-lipid ATX inhibitors

FIGURE 2
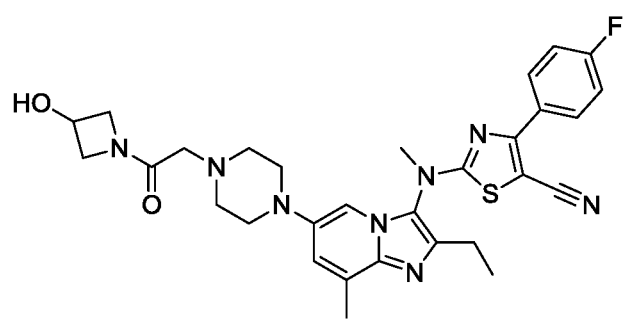
Galapagos 2015
Galapagos
$IC_{50}$ = 100 nM - 500 nM
Molecular Weight = 588.69
logp = 3.6
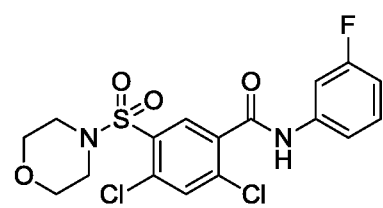
918013
The University of Tennessee
$IC_{50}$ = 116 nM
Molecular Weight = 433.28
logp = 2.99

FIGURE 3
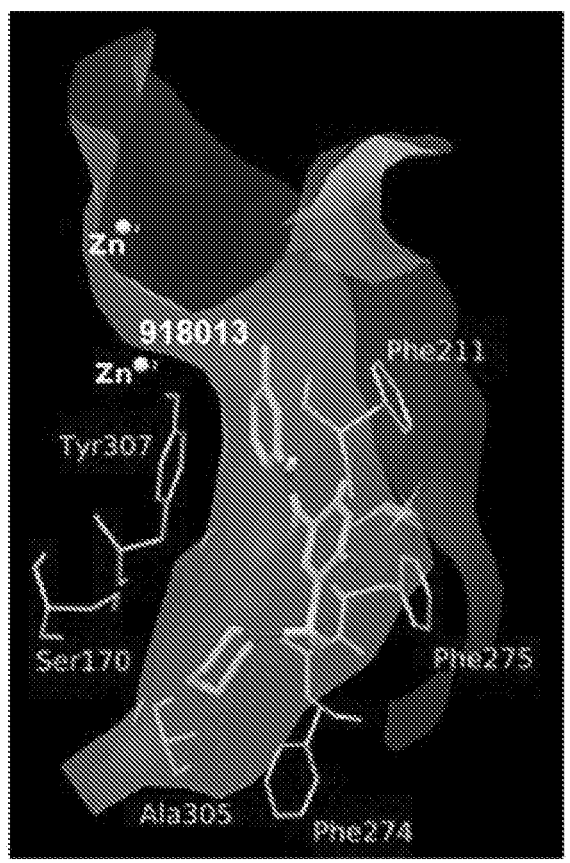
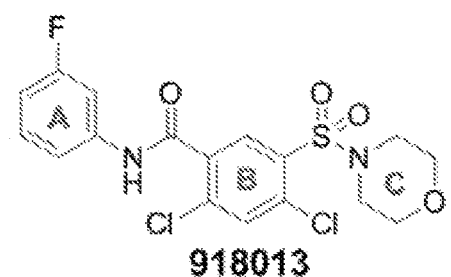

AUTOTAXIN INHIBITORS

RELATED APPLICATION

This application is a 35 U.S.C. § 371 filing of International Application No. PCT/US2017/035629, filed on Jun. 2, 2017, which claims priority to U.S. Provisional Patent Application No. 62/345,472, filed on Jun. 3, 2016. The entire contents of these applications are incorporated by reference herein, in their entirety.

GOVERNMENT SUPPORT

The invention was made with research funds from the Department of Veterans Affairs and government support under Grant No. CA092160 awarded by the National Institute of Health. The government has certain rights in the invention.

BACKGROUND

Autotaxin (ATX), a member of the ecto-nucleotide pyrophosphatase and phosphodiesterase (NPP) family, is primarily known to catalyze the hydrolysis of lysophosphatidylcholine (LPC) resulting in the production of the growth-factor-like bioactive phospholipid lysophosphatidic acid (LPA).[1-6] LPA elicits a number of cellular responses, including cell proliferation and migration, resistance to apoptosis, chemotaxis, neuropathic pain as well as platelet aggregation, by activating a set of six G-protein-coupled receptors (GPCRs) $LPA_{1-6}$.[2,4,7] The ATX-LPA signaling pathway has been connected with a number of diseases, including cancer growth, metastasis, and therapeutic resistance, fibrotic diseases, neuropathic pain, inflammation, autoimmune diseases, as well as cardiovascular diseases.[1,2,4,6-11] In recent years, research efforts have been reported both from industry and academia on the development of potent ATX inhibitors, with the ability to modulate the LPA production, as an emerging class of drug entities for potential therapeutic uses.[2,4,7,12] Several medicinal chemistry efforts have identified chemical entities with ATX inhibitory activity.[7,13-16] These efforts have resulted in a number of novel ATX inhibitors belonging to two distinct families, a) lipid-like ATX inhibitors, that mimic the natural LPC as well as LPA phospholipids and b) non-lipid ATX inhibitors (FIG. 1,[2-7, 12-17]). Despite these efforts over the years, limited success has been achieved in preclinical development of ATX inhibitor drug candidates.[2,7] There remains a considerable unmet need to develop novel ATX inhibitors.

SUMMARY

Accordingly, the present disclosure provides ATX inhibitors, and pharmaceutically acceptable salts thereof, collectively referred to as "compounds of the invention." In one aspect, provided herein is a compound having the structure of formula (I):

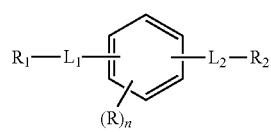

(I)

or a pharmaceutically acceptable salt thereof, wherein: $L_1$ is a divalent radical selected from $-SO_2-$ and $-NR_4-$; $L_2$ is absent or is a divalent radical selected from $-C(S)NH-$, $-CH_2N(R_3)-$, $-OC(O)NH-$, $-NHC(O)O-$, $-NHC(O)NH-$ and $-N(R_3)-SO_2-$; R, for each occurrence, is independently selected from $C_1$-$C_6$ alkyl, $C_1$-$C_6$ alkoxy and halogen; $R_1$ is heterocycloalkyl; $R_2$ is aryl or heteroaryl; $R_3$ is selected from hydrogen, $C_1$-$C_6$ alkyl, $-SO_2(C_1$-$C_6$ alkyl) and $-SO_2$(aryl); $R_4$ is selected from hydrogen, $C_1$-$C_6$ alkyl, $-CH_2CO_2H$, $CH_2CONH_2$, $CH_2C(O)NH(C_1$-$C_6$ alkyl), $-CN$, $-C(O)C_1$-$C_6$ alkyl, $-C(O)NHC_1$-$C_6$ alkyl, $-P(O)_2OH$, $-S(O)_2OH$, $-SO_2(C_1$-$C_6$ alkyl) and $-SO_2$(aryl); and n is 0, 1, 2 or 3.

In another aspect, provided herein is a compound having the structure of formula (V):

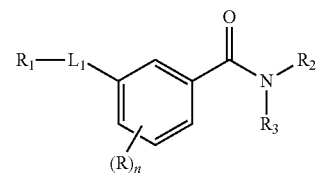

(V)

or a pharmaceutically acceptable salt thereof, wherein: $L_1$ is a divalent radical selected from $-SO_2-$ and $-NR_4-$; R, for each occurrence, is independently selected from $C_1$-$C_6$ alkyl, $C_1$-$C_6$ alkoxy and halogen; $R_1$ is heterocycloalkyl;

$R_2$ is selected from phenyl and heteroaryl, $R_2$ is substituted with 2-5 substituents independently selected from bromine, chlorine, fluorine, $-CN$, $-CO_2H$ and $-CO_2(C_1$-$C_6$ alkyl) or heteroaryl; $R_3$ is selected from hydrogen, $C_1$-$C_6$ alkyl, $-SO_2(C_1$-$C_6$ alkyl) and $-SO_2$(aryl);

$R_4$ is selected from hydrogen, $C_1$-$C_6$ alkyl, $-CH_2CO_2H$, $CH_2CONH_2$, $CH_2C(O)NH(C_1$-$C_6$ alkyl), $-CN$, $-C(O)C_1$-$C_6$ alkyl, $-C(O)NHC_1$-$C_6$ alkyl, $-P(O)_2OH$, $-S(O)_2OH$, $-SO_2(C_1$-$C_6$ alkyl) and $-SO_2$(aryl); and n is 0, 1, 2 or 3; provided that when $R_1$ is morpholin-1-yl, $R_3$ is hydrogen and $R_2$ is phenyl, the phenyl is substituted with 3-5 substituents independently selected from bromine, chlorine, fluorine, $-CN$, $-CO_2H$ and $-CO_2(C_1$-$C_6$ alkyl) or heteroaryl.

In another aspect, provided herein is a pharmaceutical composition comprising a compound of the invention, and a pharmaceutically acceptable carrier.

In another aspect, provided herein is a method of treating a disorder selected from the group consisting of a fibrotic disease, neuropathic pain, inflammation, an autoimmune disease, and cardiovascular disease in a subject in need of treatment, comprising administering to the subject a compound of the invention, such that the disorder is treated.

In another aspect, provided herein is a method of treating cancer in a subject in need of such treatment, comprising administering to the subject a compound of the invention, such that the disorder is treated. In one embodiment, the cancer is breast cancer. In another embodiment, the cancer is resistant to one or more chemotherapeutic drugs.

In another aspect, provided herein is a method of inhibiting ATX in a subject, comprising administering to the subject a compound of the invention.

BRIEF DESCRIPTION OF THE DRAWINGS

FIG. 1 depicts lipid-like and non-lipid ATX inhibitors.

FIG. 2 depicts non-acidic head group non-lipid ATX inhibitors.

FIG. 3 depicts the binding pose (low energy conformation) of 918013 in the active site of ATX crystal structure (PDB 2XRG).[18] The enzyme surface is shown in the red-white-blue color ramp (electrostatic potential). Selected key residue side chains are shown as sticks in green. The Zn(II) ions at the catalytic site are shown as blue spheres. Interactions between enzyme residues and the inhibitors are shown in dashed lines.

DETAILED DESCRIPTION

Figure 4:
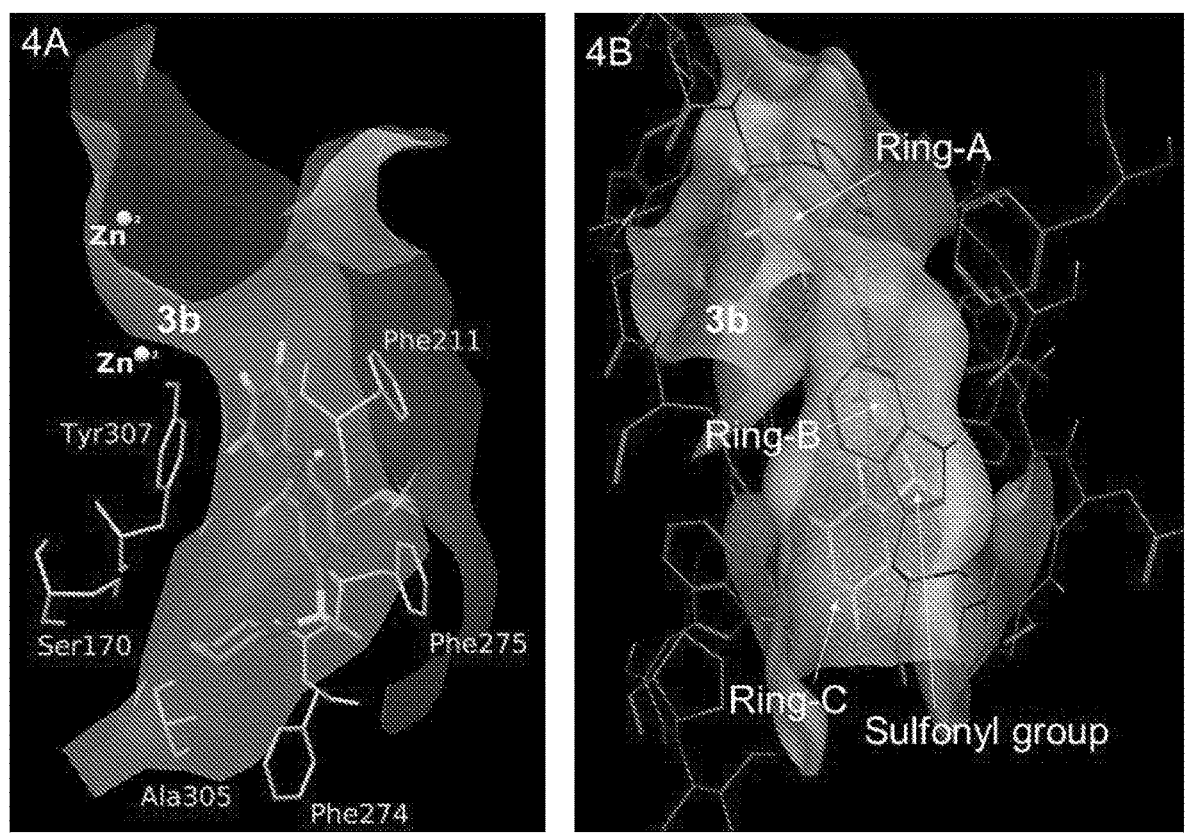
FIG. 4 depicts the binding pose (low energy conformation) of 3b in the ATX crystal structure (PDB 2XRG).

Various structural features of the lipid-like ATX inhibitors may be counterproductive for the potential clinical development of this set of molecules. Primarily, one of the biggest challenges of this set of molecules is the unsuitable partition coefficients to be a drug candidate (log p>5, FIG. 1, lipid-like ATX inhibitors), limiting their therapeutic utility.[2,13] Additionally, the presence of chiral centers, which play an important factor in enzyme inhibition, in numerous lipid-like ATX inhibitors may lead to difficulties in industrial scale production. One of the most significant developments in this field is the discovery of the ATX crystal structure with an active site inhibitor HA 155 crystalized in it, providing insight into the potential active site surface of ATX.[18-21] Elucidation of the ATX crystal structure expedited rational discovery of a new generation of small molecule drug-like non-lipid ATX inhibitors with pharmacological properties in the acceptable range (FIG. 1).[2,5,7,13,15] Most of the recently developed non-lipid ATX inhibitors, including PF 8380, HA 155, Novartis 2014 as well as PharmAkea 2015 (FIG. 1), have similar structural features and mode of binding.[4,7,12] These molecules contain an acid or acid-like moiety, to interact with one of the $Zn^{2+}$ ions at the catalytic site of ATX, a core spacer, and a hydrophobic tail, to be accommodated within the hydrophobic pocket of ATX.[4,7,12] This may be attributed to the potential issues of toxicity and off-target effects with of acidic moiety.[7] Thus, the synthetic approaches disclosed herein have focused on developing small molecule non-lipid ATX inhibitors without an acidic moiety. In silico searching was used to identify a small molecule ATX inhibitor, 918013 (FIG. 2), which exerts its catalytic activity by binding in the hydrophobic pocket remote from the catalytic site, and lacks an acidic moiety.[2,5] Compound 918013, even without an acidic head group, shows the same pharmacological and biological effects as compounds that block the catalytic site due to its interference with the binding of the hydrophobic parts of the substrate.[2,5,7] Additionally, anti-metastatic and anti-invasive effects of 918013, as well as positive results in off-target analysis, strongly underscore the utility of this chemical core. There remains a considerable unmet need to develop novel ATX inhibitors. In various aspects and embodiments, provided herein are ATX inhibitors referred to as compounds of the invention. In one embodiment, the compounds of the invention have one or more of the following characteristics: a) lack an acidic moiety; b) lack a chiral center; and c) have a molecular weight less than 500 Dalton. In one embodiment, the compounds of the invention have all of the following characteristics: a) lack of an acidic moiety; b) lack of a chiral center; and c) a molecular weight less than 500 Dalton.

Definitions

As used herein, the term "alkyl" refers to a fully saturated branched or unbranched hydrocarbyl moiety. The alkyl can comprise 1 to 20 carbon atoms, 1 to 16 carbon atoms, 1 to 10 carbon atoms, 1 to 7 carbon atoms, 1 to 6 carbons, 1 to 4 carbons, or 1 to 3 carbon atoms. In a particular embodiment, the alkyl comprises 1-6 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neo-pentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight-chain or branching) of a particular range of carbons. For example, the expression $C_1$-$C_4$-alkyl includes, but is not limited to, methyl, ethyl, propyl, butyl, iso-propyl, tert-butyl and iso-butyl.

"Alkoxy" refers to those alkyl groups, having from 1 to 20 carbon atoms, 1 to 16 carbon atoms, 1 to 10 carbon atoms, 1 to 7 carbon atoms, 1 to 6 carbons, 1 to 4 carbons, 1 to 3 carbon atoms, or one carbon atom, attached to the remainder of the molecule via an oxygen atom. The alkyl portion of an alkoxy may be linear, cyclic, branched, or a combination thereof. Examples of alkoxy groups include methoxy, ethoxy, isopropoxy, butoxy, cyclopentyloxy, and the like. An alkoxy group can also be represented by the following formula: —$OR^a$, where $R^a$ is the "alkyl portion" of an alkoxy group.

The term "heterocycloalkyl" refers to a five- to ten-member, partially or fully saturated nonaromatic heterocylic group containing at least one heteroatom such as O, S, or N. In one embodiment, "heterocycloalkyl" refers to a cyclic group having 4-5 carbon atoms and 1-2 heteroatoms selected from O and N in the ring structure. Common examples of heterocycloalkyl radicals include piperidinyl, morpholinyl, piperazinyl, and pyrrolidinyl. Attachment of a heterocycloalkyl substituent can occur via a carbon atom or via a heteroatom.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "halogen" refers to a fluorine, chlorine, bromine, iodine, or astatine atom. Additionally, terms such as "haloalkyl", are meant to include monohaloalkyl and perhaloalkyl. For example, the term "halo-$C_{1-4}$-alkyl" is meant to include, but not be limited to, trifluoromethyl, 2,2,2-trifluoroethyl, 4-chlorobutyl, 3-bromopropyl, and the like. The prefix "perhalo" refers to the respective group wherein all available valences are replaced by halo groups. For example "perhaloalkyl" includes —$CCl_3$, —$CF_3$, —$CCl_2CF_3$, and the like. The terms "perfluoroalkyl" and "perchloroalkyl" are a subsets of perhaloalkyl wherein all available valences are replaced by fluoro and chloro groups, respectively. Non-limiting examples of perfluoroalkyl include —$CF_3$, and —$CF_2CF_3$. Non limiting examples of perchloroalkyl include —$CCl_3$ and —$CCl_2CCl_3$.

Compounds of the Invention

In one aspect, provided herein is a compound having the structure of formula (I):

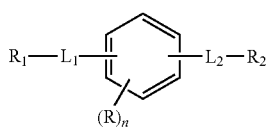

(I)

or a pharmaceutically acceptable salt thereof, wherein: $L_1$ is a divalent radical selected from —$SO_2$— and —$NR_4$—; $L_2$ is absent or is a divalent radical selected from —C(S)NH—, —$CH_2N(R_3)$—, —OC(O)NH—, —NHC(O)O—, —NHC(O)NH— and —$N(R_3)$—$SO_2$—; R, for each occurrence, is independently selected from $C_1$-$C_6$ alkyl, $C_1$-$C_6$ alkoxy, and halogen; $R_1$ is heterocycloalkyl; $R_2$ is aryl or heteroaryl; $R_3$ is selected from hydrogen, $C_1$-$C_6$ alkyl, —$SO_2(C_1$-$C_6$ alkyl) and —$SO_2$(aryl); $R_4$ is selected from hydrogen, $C_1$-$C_6$ alkyl, —$CH_2CO_2H$, $CH_2CONH_2$, $CH_2C(O)NH(C_1$-$C_6$ alkyl), —CN, —C(O)$C_1$-$C_6$ alkyl, —C(O)NH$C_1$-$C_6$ alkyl, —P(O)$_2$OH, —S(O)$_2$OH, —$SO_2(C_1$-$C_6$ alkyl) and —$SO_2$(aryl); and n is 0, 1, 2, or 3.

In one embodiment, the compound of formula (I) has the structure of formula (II), or a pharmaceutically acceptable salt thereof.

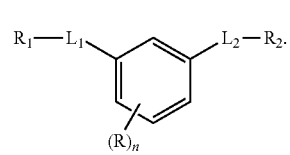

(II)

In one embodiment, the compound of formula (II) has the structure of formula (III), or a pharmaceutically acceptable salt thereof.

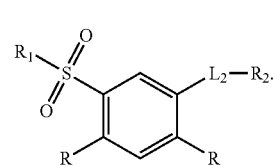

(III)

In another embodiment, the compound of formula (II) has the structure of formula (IV), or a pharmaceutically acceptable salt thereof.

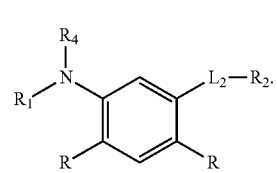

(IV)

In one embodiment, the compound of formula (III) is selected from the group consisting of:

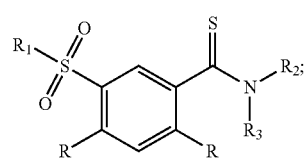

(III-1)

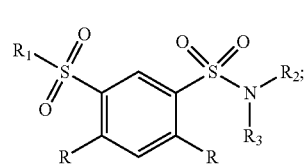

(III-2)

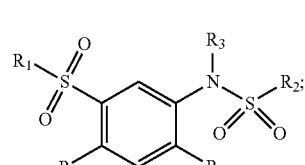

(III-3)

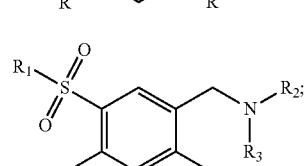

(III-4)

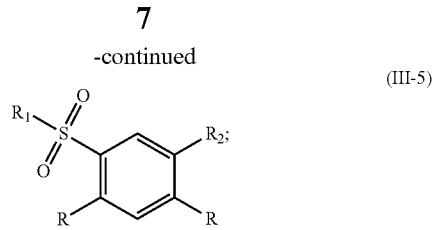

(III-5)

and pharmaceutically acceptable salts thereof.

In one embodiment of the compounds of the invention, each R is independently halogen. In a particular embodiment, each R is chlorine.

In another embodiment of the compounds of the invention, $R_1$ is morpholin-1-yl. In another embodiment, $R_1$ is 1-methyl-piperazinyl.

In one embodiment of the compounds of the invention, $R_2$ is phenyl substituted with 1-4 substituents independently selected from bromine, chlorine, fluorine, —CN, —CO$_2$H and —CO$_2$(C$_1$-C$_6$ alkyl). In another embodiment, $R_2$ is heteroaryl substituted with 1-4 substituents independently selected from bromine, chlorine, fluorine, —CN, —CO$_2$H and —CO$_2$(C$_1$-C$_6$ alkyl).

In one embodiment of the compounds of the invention, $R_3$ is hydrogen.

In one embodiment, the compound of formula (III-1) has the structure of formula (III-1A), or a pharmaceutically acceptable salt thereof:

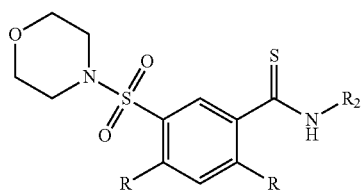

(III-1A)

wherein: R, for each instance, independently is halogen; and $R_2$ is phenyl, substituted with 1-4 substituents independently selected from bromine, chlorine, fluorine, and —CN.

In one embodiment of formula (III-1A), or a pharmaceutically acceptable salt thereof, each R is chlorine, and $R_2$ is phenyl, substituted with 1-4 substituents selected from bromine, chlorine, fluorine, and —CN.

In another aspect, provided herein is a compound having the structure of formula (V):

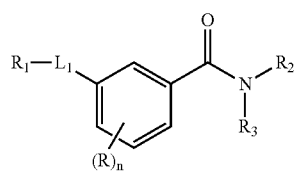

(V)

or a pharmaceutically acceptable salt thereof,
wherein: $L_1$ is a divalent radical selected from —SO$_2$— and —NR$_4$—; R, for each occurrence, is independently selected from C$_1$-C$_6$ alkyl, C$_1$-C$_6$ alkoxy and halogen; $R_1$ is heterocycloalkyl;
$R_2$ is selected from phenyl and heteroaryl, wherein $R_2$ is substituted with 2-5 substituents independently selected from bromine, chlorine, fluorine, —CN, —CO$_2$H and —CO$_2$(C$_1$-C$_6$ alkyl) or heteroaryl; $R_3$ is selected from hydrogen, C$_1$-C$_6$ alkyl, —SO$_2$(C$_1$-C$_6$ alkyl) and —SO$_2$(aryl); $R_4$ is selected from hydrogen, C$_1$-C$_6$ alkyl, —CH$_2$CO$_2$H, CH$_2$CONH$_2$, CH$_2$C(O)NH(C$_1$-C$_6$ alkyl), —CN, —C(O)C$_1$-C$_6$ alkyl, —C(O)NHC$_1$-C$_6$ alkyl, —P(O)$_2$OH, —S(O)$_2$OH, —SO$_2$(C$_1$-C$_6$ alkyl) and —SO$_2$(aryl); and n is 0, 1, 2 or 3; provided that, when $R_1$ is morpholin-1-yl, $R_3$ is hydrogen and $R_2$ is phenyl, the phenyl is substituted with 3-5 substituents independently selected from bromine, chlorine, fluorine, —CN, —CO$_2$H, and —CO$_2$(C$_1$-C$_6$ alkyl) or heteroaryl.

In one embodiment of formula (V), or a pharmaceutically acceptable salt thereof, $L_1$ is —SO$_2$—. In another embodiment, the compound of formula (V) has the structure of formula (V-1):

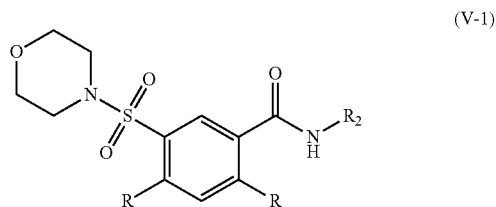

(V-1)

or a pharmaceutically acceptable salt thereof,
wherein: R, for each instance, independently is halogen; and $R_2$ is phenyl, substituted with 2-4 substituents independently selected from bromine, chlorine, fluorine, —CN and —CO$_2$(C$_1$-C$_6$ alkyl).

In one embodiment of formula (V-1), or a pharmaceutically acceptable salt thereof, each R is chlorine and wherein $R_2$ is phenyl substituted with 3-4 substituents selected from bromine, chlorine, fluorine, and —CN.

In another embodiment, the compound of formula (V) has the structure of formula (V-2):

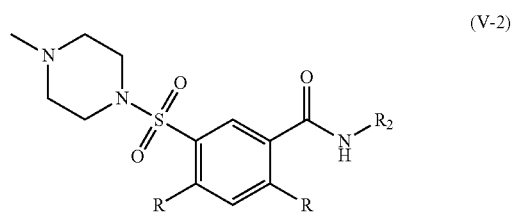

(V-2)

or a pharmaceutically acceptable salt thereof,
wherein: R, for each instance, independently is halogen; and $R_2$ is phenyl, substituted with 2-3 substituents independently selected from bromine, chlorine, fluorine, —CN and —CO$_2$(C$_1$-C$_6$ alkyl).

In one embodiment of formula (V-2), or a pharmaceutically acceptable salt thereof, each R is chlorine and wherein $R_2$ is phenyl substituted with 2-3 substituents selected from bromine, chlorine, fluorine, and —CN.

In one embodiment of formula (V), or a pharmaceutically acceptable salt thereof, $L_1$ is —NR$_4$—. In another embodiment, the compound of formula (V) has the structure of formula (V-3):

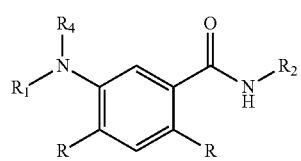
(V-3)
or a pharmaceutically acceptable salt thereof.
In another aspect, the compound of the invention is selected from the group consisting of
SB1-85 (3b)
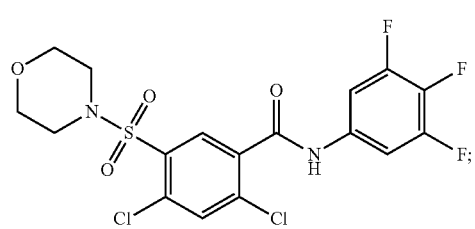
SB1-94 (5)
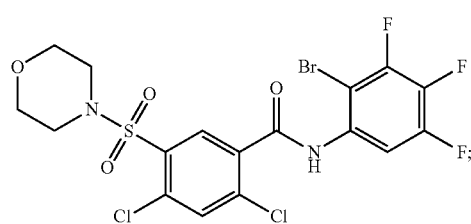
SB1-89 (3a)
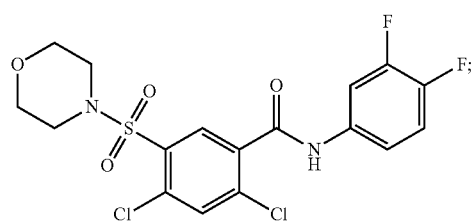
SB1-93 (14)
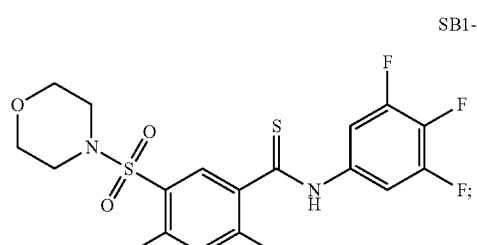
SB1-130 (3g)
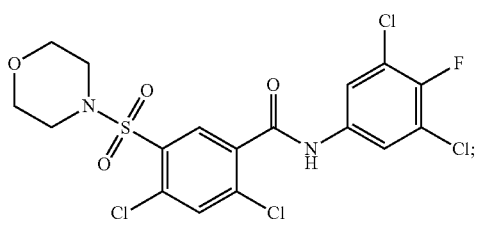
SB1-140 (28b)
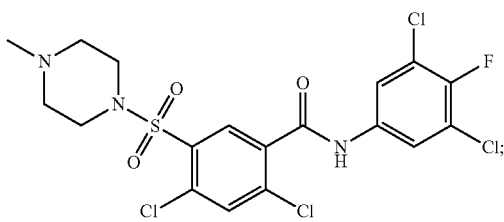
SB1-139 (28a)
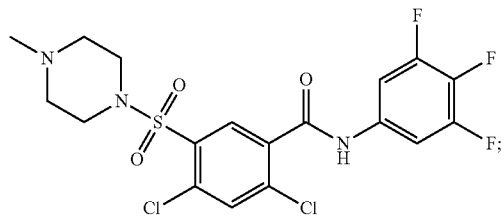
SB1-146 (13)
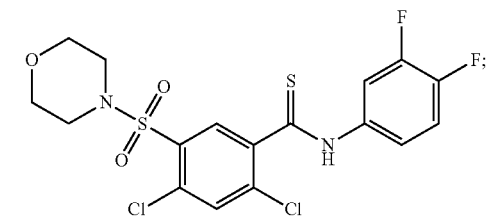
SB1-145 (15)
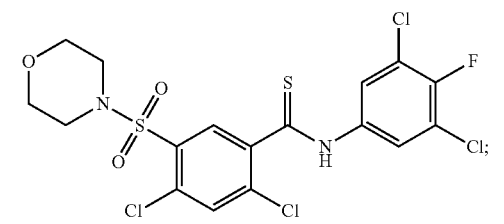
SB1-131 (3f)
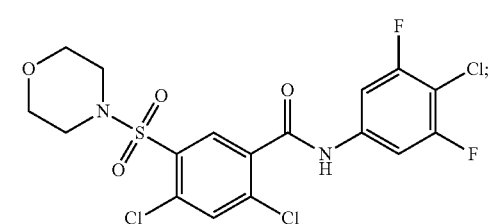
SB1-142 (29)
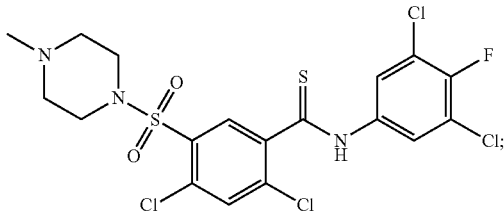

-continued
SB1-79 (12)
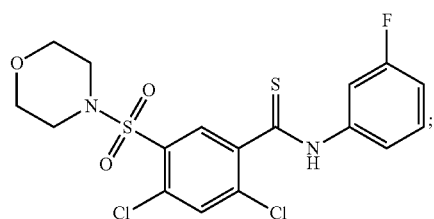
SB1-112 (3h)
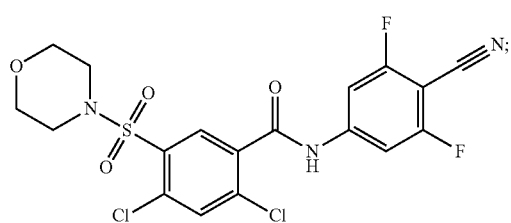
SB1-92 (11)
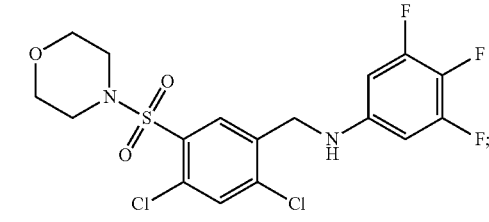
SB1-137 (3i)
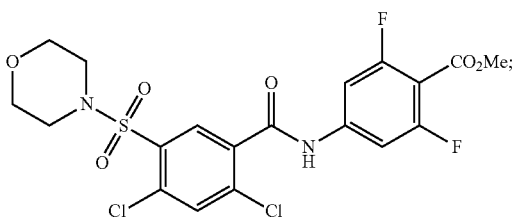
SB1-111 (3c)
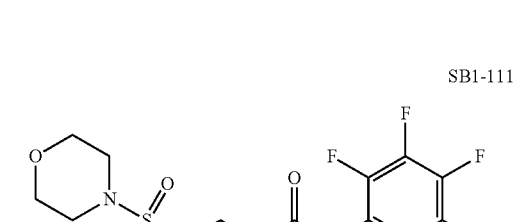
SB1-91 (10)
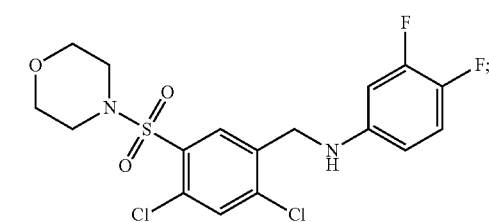
-continued
SB1-98B (20)
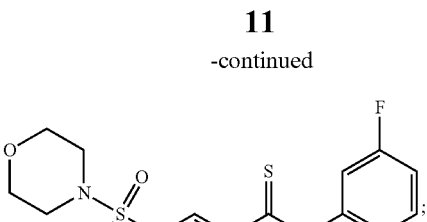
SB1-98A (19)
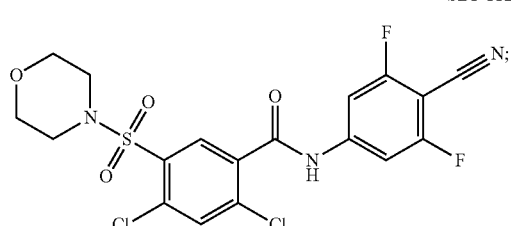
SB1-100 (8)
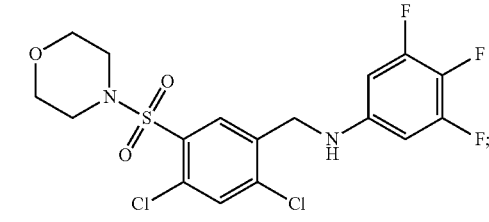
SB1-102 (7)
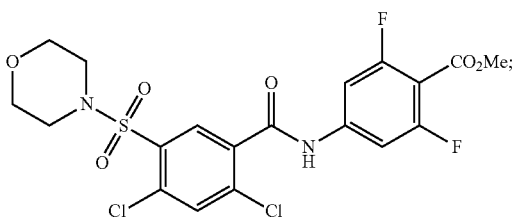
SB1-104 (23)
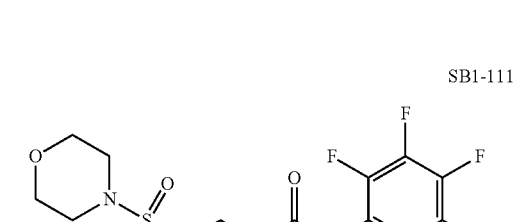
SB1-105 (22)
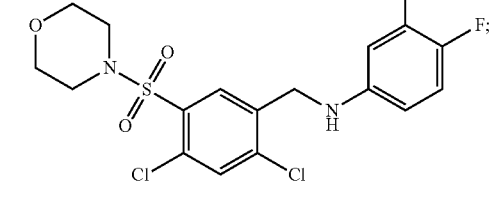

SB1-106 (3d)

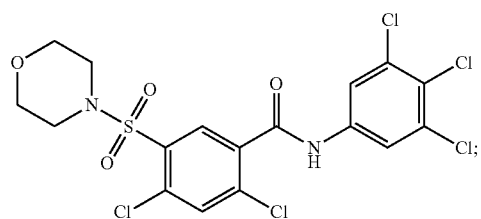

SB1-107

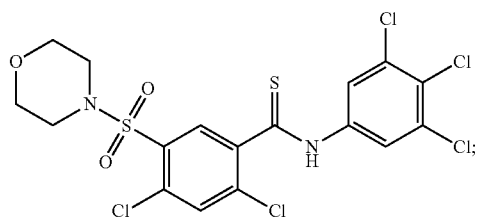

SB1-113 (9)

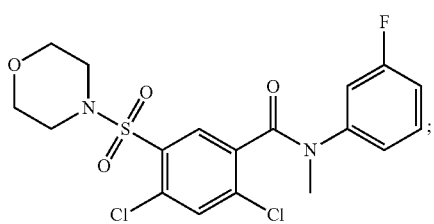

SB1-122 (25)

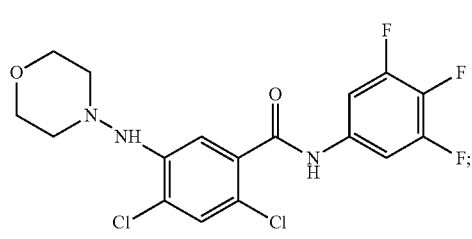

SB1-138 (4)

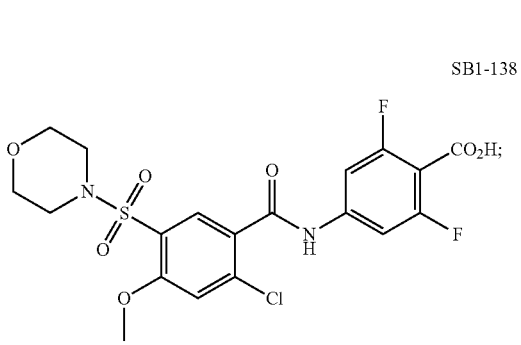

SB1-141 (26a)

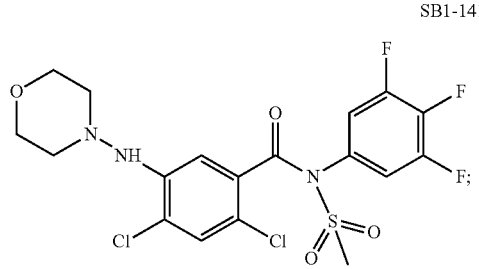

(3e)

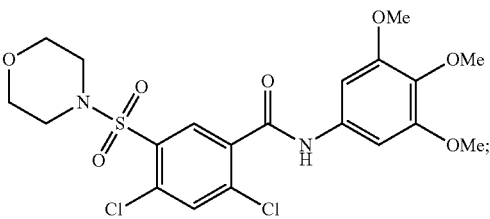

and pharmaceutically acceptable salts thereof.

In a particular embodiment, the compound of the invention is SB1-85 (3b), or a pharmaceutically acceptable salt thereof.

Unless otherwise indicated, the compounds of the invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

Compounds of the invention include all pharmaceutically acceptable isotopically-labeled analogues, wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{121}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of the invention, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described in the accompanying Examples using an appropriate isotopically-labeled reagents in place of the non-labeled reagent previously employed.

A "pharmaceutically acceptable salt," as used herein, and unless otherwise indicated, includes salts of acidic and basic groups which may be present in the compounds of the present invention. Such salts may be formed, for example, as acid addition salts, preferably with organic or inorganic acids, upon reaction with a basic nitrogen atom. Suitable inorganic acids are, for example, mineral acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates.

Pharmaceutical Compositions

In one aspect, provided herein is a pharmaceutical composition comprising a compound of the invention, and a pharmaceutically acceptable carrier. Compounds of the invention are suitable as active agents in compositions that are effective particularly for treating diseases and disorders selected from the group consisting of cancer (e.g., breast cancer), a fibrotic disease, neuropathic pain, inflammation, an autoimmune disease, and cardiovascular disease in subjects in need of treatment.

The term "pharmaceutical composition" is defined herein to refer to a mixture or solution containing at least one therapeutic agent to be administered to a subject, e.g., a mammal or human, in order to prevent or treat a particular disease or condition affecting the mammal or human.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

In various embodiments, pharmaceutical compositions of compounds of the invention comprise a pharmaceutically effective amount of the compound of the invention together with one or more pharmaceutically acceptable excipients, carriers, fillers, diluents and the like.

A "pharmaceutically effective amount" of the compound is that amount necessary or sufficient to treat or prevent a protein kinase-associated disorder, e.g. prevent the various morphological and somatic symptoms of a disorder and/or a disease or condition described herein. In an example, an effective amount of a compound of the invention is the amount sufficient to treat cancer (e.g., breast cancer) in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The pharmaceutical compositions described herein may contain, from about 0.1% to about 99.9%, preferably from about 1% to about 60%, of the therapeutic agent(s). Suitable pharmaceutical compositions for enteral (e.g., oral or rectal) or parenteral (e.g., intravenous or intramuscular) administration are, for example, those in unit dosage forms, such as tablets, capsules or suppositories, or ampoules. If not indicated otherwise, these are prepared in a manner known per se, for example by means of various conventional mixing, comminution, direct compression, granulating, sugar-coating, dissolving, lyophilizing processes, or fabrication techniques readily apparent to those skilled in the art. It will be appreciated that the content of a compound contained in an individual dosage unit need not in itself constitute an effective amount since the necessary effective amount may be reached by administration of a plurality of dosage units.

Methods of Treatment

In one aspect, provided herein is a method of treating a disorder selected from the group consisting of a fibrotic disease, neuropathic pain, inflammation, an autoimmune disease, and cardiovascular disease in a subject in need of treatment, comprising administering to the subject a compound of the invention, such that the disorder is treated. In another aspect, provided herein is a method of treating cancer in a subject in need of such treatment, comprising administering to the subject a compound of the invention, such that the disorder is treated. In one embodiment, the cancer is breast cancer. In another embodiment, the cancer is resistant to one or more chemotherapeutic drugs.

In another aspect, provided herein is a method of inhibiting ATX in a subject, comprising administering to the subject a compound of the invention.

The term "treating" or "treatment" as used herein comprises a treatment relieving, reducing or alleviating at least one symptom in a subject or affecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease), and/or reduce the risk of developing or worsening a disease. The term "prevent," "preventing," or "prevention" as used herein comprises the prevention of at least one symptom associated with or caused by the state, disease or disorder being prevented.

The term "subject" or "patient" as used herein includes animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats and transgenic non-human animals. In the particular embodiment, the subject is a human, e.g., a human suffering from, at risk of suffering from, or potentially capable of suffering from cancer.

The optimal dosage of a compound of the invention for the treatment of a disease, disorder or condition disclosed herein can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

Frequency of dosage may vary depending on the compound used and the particular condition to be treated or prevented. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

EXAMPLES

Example 1: Chemistry

The three rings in 918013 were designated the A-ring, B-ring, and C-ring, as shown in the FIG. 3. Our previous screening experiments and molecular modelling findings suggested that benzenesulfonamide analogue, 918013, binds into the hydrophobic pocket of ATX without protruding into the catalytic site as shown in FIG. 3. In FIG. 3, the enzyme surface is shown in the red-white-blue color ramp (electrostatic potential). Selected key residue side chains are shown as sticks in green. The Zn(II) ions at the catalytic site are shown as blue spheres. Interactions between enzyme residues and the inhibitors are shown in dashed lines. Docking was conducted using the Glide application within Schrödinger Molecular Modeling Suite 2014 (Schrödinger, LLC, New York, N.Y., 2014.). Crystal structure of a ATX complex (PDB code: 2XRG) was used for the docking, and all ligands were prepared using LigPrep application. The docking figures were prepared using Maestro of the Schrödinger Molecular Modeling Suite.

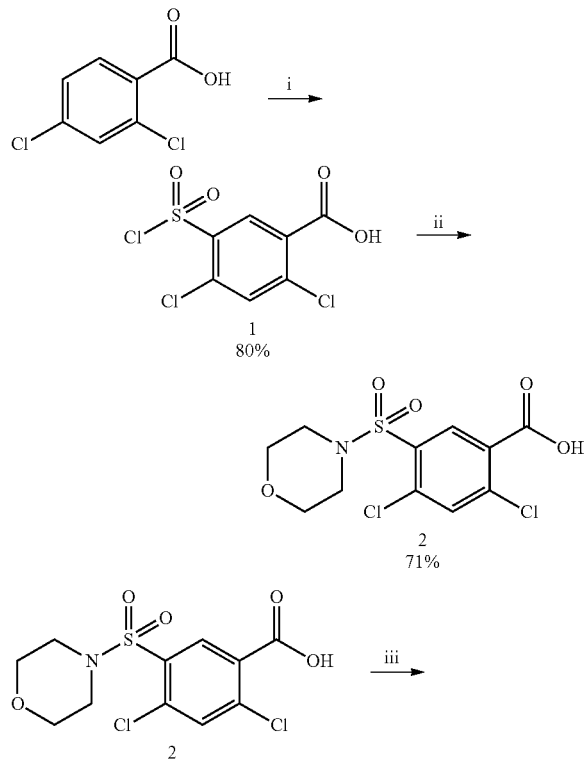

Scheme 1. Design and synthesis of ring-A modified benzene sulfonamide analogues.

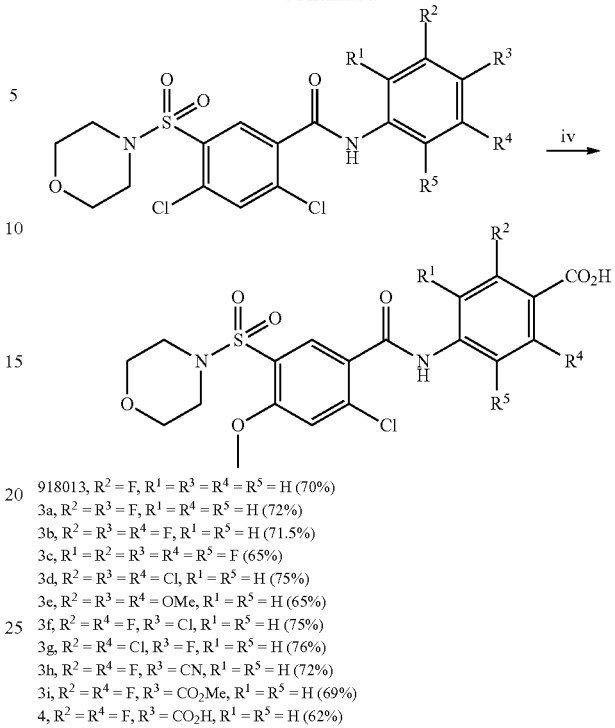

918013, $R^2 = F$, $R^1 = R^3 = R^4 = R^5 = H$ (70%)
3a, $R^2 = R^3 = F$, $R^1 = R^4 = R^5 = H$ (72%)
3b, $R^2 = R^3 = R^4 = F$, $R^1 = R^5 = H$ (71.5%)
3c, $R^1 = R^2 = R^3 = R^4 = R^5 = F$ (65%)
3d, $R^2 = R^3 = R^4 = Cl$, $R^1 = R^5 = H$ (75%)
3e, $R^2 = R^3 = R^4 = OMe$, $R^1 = R^5 = H$ (65%)
3f, $R^2 = R^4 = F$, $R^3 = Cl$, $R^1 = R^5 = H$ (75%)
3g, $R^2 = R^4 = Cl$, $R^3 = F$, $R^1 = R^5 = H$ (76%)
3h, $R^2 = R^4 = F$, $R^3 = CN$, $R^1 = R^5 = H$ (72%)
3i, $R^2 = R^4 = F$, $R^3 = CO_2Me$, $R^1 = R^5 = H$ (69%)
4, $R^2 = R^4 = F$, $R^3 = CO_2H$, $R^1 = R^5 = H$ (62%)

i. ClSO$_3$H, 12 hrs. reflux, ii. morpholine, Et$_3$N, R.T. 12 hrs. iii. a) SOCl$_2$, DMF (cat), 12 hrs. R.T. (b) substituted-aniline, pyridine, 12 hrs. R.T. iv) LiOH, MeOH/THF Compound 918013, was synthesized following the strategy shown in Scheme 1 in good yield (70%). First, the number of fluorine substituents on the A-ring was increased. The 3,4-di-fluoro analogue, 3a, was prepared as well as the 3,4,5-tri-fluoro analogue, 3b, following the same synthetic strategy as depicted in Scheme 1. These compounds were tested for ATX inhibitory activity. Surprisingly, the simple manipulation of aromatic substituents resulted in four-fold and thirteen-fold IC$_{50}$ improvements in 3a (IC$_{50}$=31 nM) and 3b (IC$_{50}$=9 nM), respectively, as shown in Table 1. Without being bound by any particular theory, one interpretation of this result is that the higher the number of fluorine atom on ring A, the greater the electron deficiency of ring A, and, therefore, the stronger the dipole-induced dipole interactions between ring A and the hydrophobic pocket. The stronger interactions, in turn, contribute to improved IC$_{50}$ values.

TABLE 1

A-ring Structure-activity data

| Cpds | IC$_{50}$ (nM ± SD) vs FS-3 | pNP-TMP Inhibition | Mechanism | logp | Molecular Weight |
| --- | --- | --- | --- | --- | --- |
| 918013 | 116.75 ± 1.97 | None | Competitive | 2.99 | 433.28 |
| 3a | 31.47 ± 2.11 | None | ND | 3.17 | 451.27 |
| 3b | 9.32 ± 0.16 | None | Competitive | 3.23 | 469.26 |
| 3c | 1,034.16 ± 119.65 | None | ND | 3.67 | 505.24 |
| 3d | >1,000 | None | ND | 4.35 | 518.63 |
| 3e | >1,000 | None | ND | 2.91 | 505.36 |
| 3f | 83.68 ± 0.00 | None | ND | 3.62 | 485.72 |
| 3g | 40.09 ± 0.33 | None | ND | 3.89 | 502.17 |
| 3h | 190.08 ± 13.05 | None | ND | 2.46 | 476.28 |
| 3i | 863.90 ± 51.88 | None | ND | 2.78 | 509.31 |
| 4 | >1,000 | None | ND | 2.26 | 476.83 |

Figure 5:
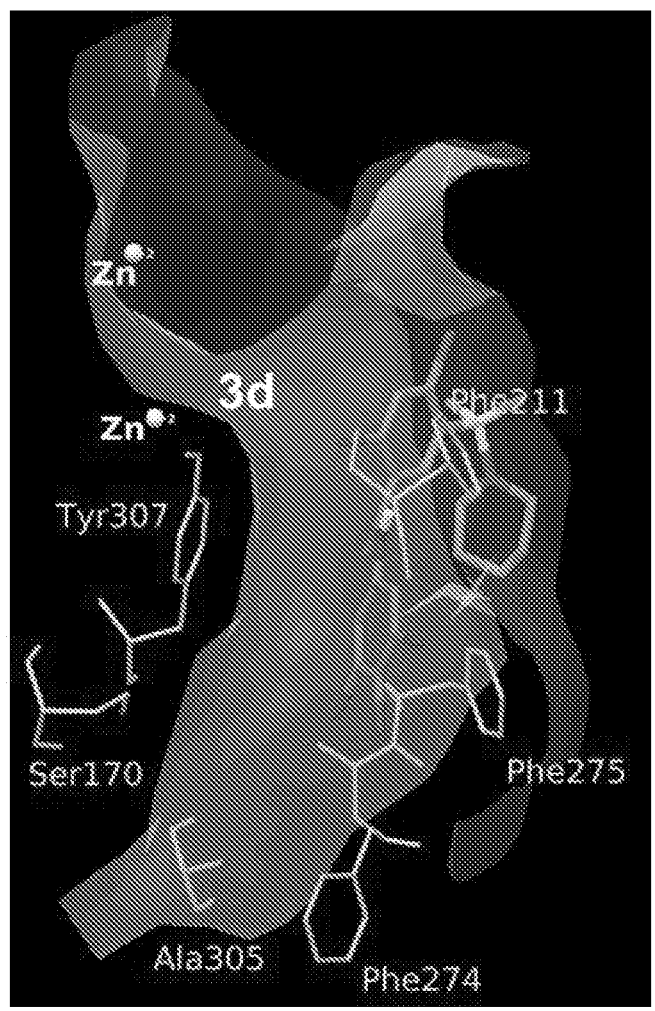
FIG. 5 depicts the binding pose (low energy conformation) of 3d in the ATX crystal structure (PDB 2XRG).

Upon obtaining the IC50 data for compound 3b, the compound was docked in the ATX crystal structure (PDB 2XRG). As shown in FIG. 4, the three fluorine substituents help 3b bind to the hydrophobic pocket more tightly than the screening hit 918013. Additionally, ring-A of 3b is oriented more towards the Tyr 307 of the receptor as well as the sulfonyl linkage is extended more towards the polar receptor surface. The penta-fluoro analogue 3c was tested for ATX inhibitory activity. Interestingly, compound 3c was not tolerated and was poorly active, possibly indicating that more than three A-ring substitutions is sterically unfavorable, and suggesting that optimal electronic and steric factors are equally important for strong binding in the hydrophobic pocket. One relatively less electron deficient 3,4,5-trichloro analogue, 3d, was prepared, as well as an electron donating 3,4,5-trimethoxy analogue, 3e. Neither of these analogues were tolerated, and both were poorly active, possibly indicating that increased steric congestion on the A-ring did not allow the molecule to be properly accommodated into the hydrophobic pocket. This indication is supported by computational docking of 3d into the ATX crystal structure (FIG. 5).

Figure 6:
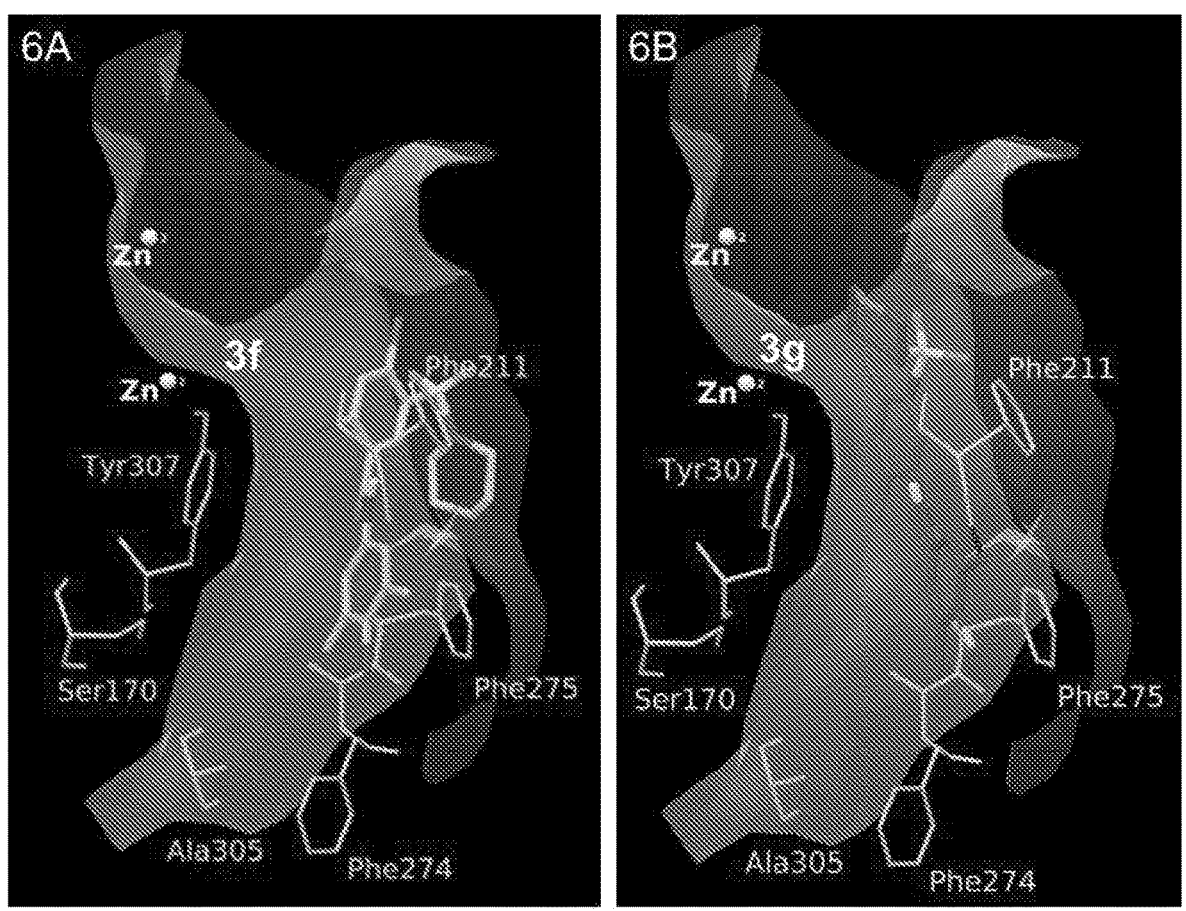
FIG. 6 depicts the binding poses of 3f (yellow) and 3g (purple) in the ATX crystal structure (PDB 2XRG).

Next, the effects of combining two different kinds of A-ring substituents on the inhibitory activity of the molecule was tested. Thus, the 3,5-difluoro-4-chloro analogue, 3f, and the 3,5-dichloro-4-fluoro analogue, 3g, were prepared and tested for ATX inhibition. Interestingly, both of the analogues were observed to be highly potent ATX inhibitors with $IC_{50}$ values of 83 nM and 40 nM, respectively. The docking poses of 3f and 3g show that 3g forms a hydrogen bonding interaction with the Phe 211 in the hydrophobic pocket and better accommodated in the hydrophobic pocket (FIG. 6). Next, 3,5-difluoro-4-cyano analogue 3h, and 3,5,-difluoro 4-methyl ester analogue 3i, were prepared and tested. 3h and 3i were less active than compound 908013, with $IC_{50}$ values of 190 nM and 863 nM, respectively.

Next, ester compound 3i was hydrolyzed into the corresponding carboxylic acid 4 and compound 4 was tested for ATX inhibitory activity. Compound 4 was relatively inactive. These finding suggests that ring A protrudes into the hydrophobic pocket of the ATX enzyme and hydrophobic electron-withdrawing substituents, like fluorine, may help create optimal electron deficiencies for the better dipole-induced dipole interactions. Next, the amide bond of compound 918013 was replaced, in order to explore the importance of amide linker in the ATX inhibition. Thus, tri-fluoro oxazole 6 was prepared through intermediate 5 as depicted in Scheme 2.

Scheme 2. Design and synthesis of amide bond modified benzene sulfonamide analogues.

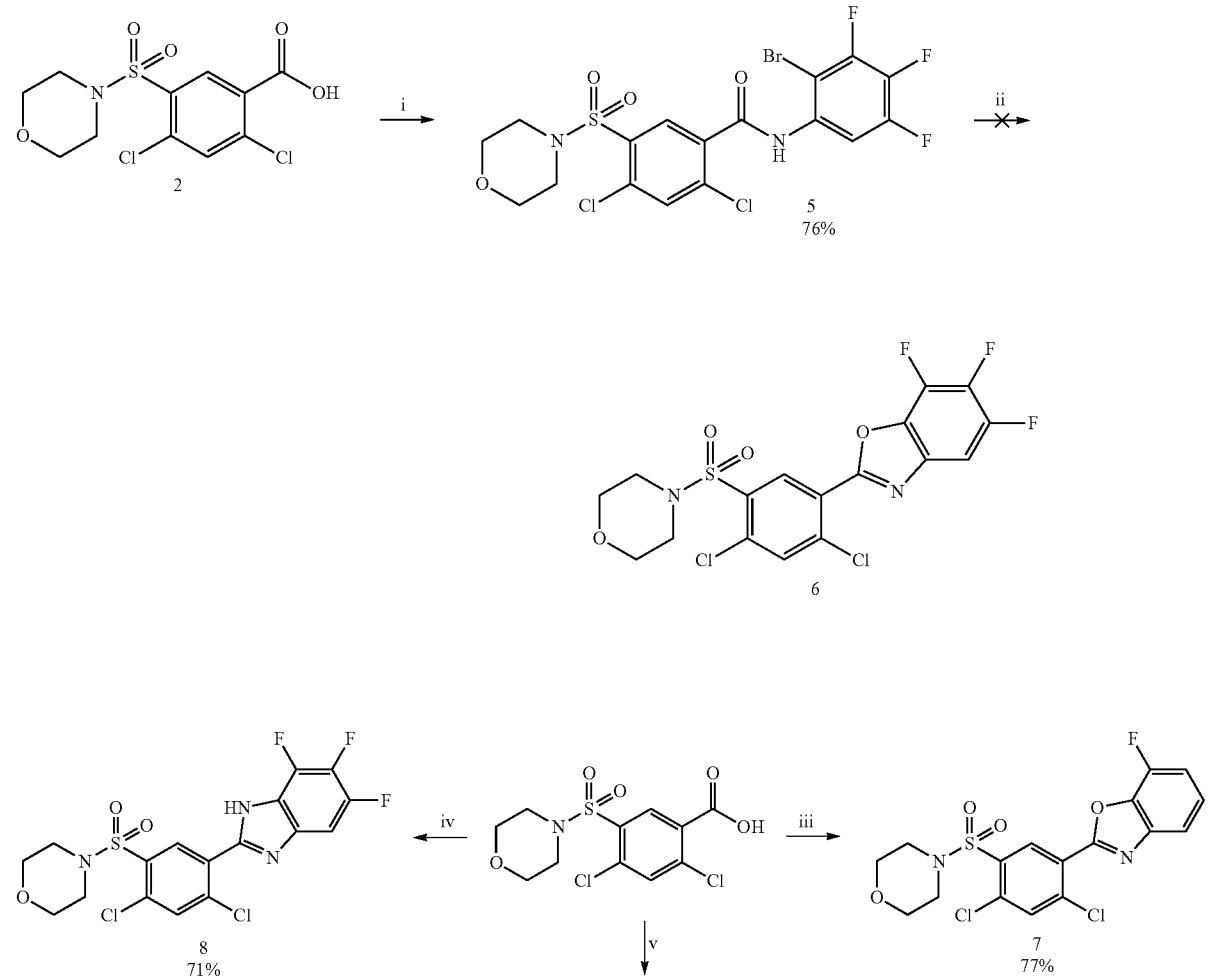

-continued

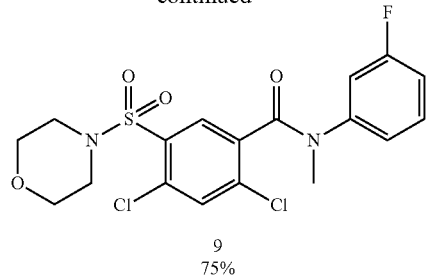

Figure 7:
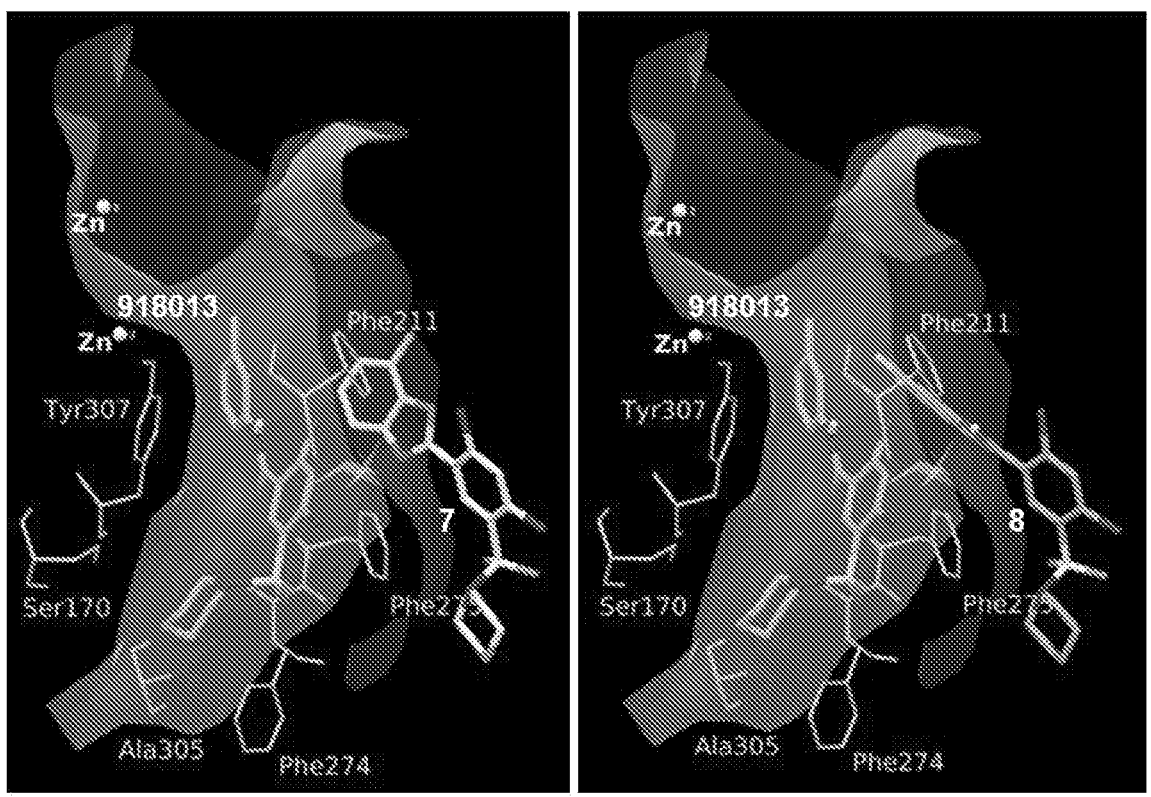
FIG. 7 depicts the binding poses of 7 (yellow) and 8 (brown) in the ATX crystal structure (PDB 2XRG).

9
75% i. a) SOCl₂, DMF (cat), b) substituted-aniline, pyridine, ii) CuI (cat), 1, 10-phenanthroline (cat), Cs₂CO₃, 2 h hrs. reflux. iii. a) SOCl₂, DMF (cat), 12 hrs. R.T. b) substituted-aniline, Et₃N. c) p-TSA. H₂O, toluene, reflux. iv. SOCl₂, DMF (cat), 12 hrs. R.T. b) substituted-aniline, Et₃N. c) POCl₃, 100 min. reflux. v. SOCl₂, DMF (cat). b) N-methyl-substituted-aniline, pyridine Intermediate 5 was obtained in good yield (76%) following the same strategy as Scheme 1. However, the synthetic procedure failed to turn intermediate 5 into desired oxazole 6. Fortunately, an alternative strategy was found, and oxazole 7, as well as imidazole 8, were prepared utilizing a commercially available amino-phenol and amino-aniline, respectively as shown in Scheme 2. In addition to the oxazole and imidazole, the N-methyl analogue 9 was also prepared as depicted in Scheme 2. The four compounds obtained from this scheme, 5, 7, 8, and 9, were tested for the ATX inhibition as shown in the Table 2. Compound 5 showed strong ATX inhibition, however, to a lesser extent than the tri-fluoro compound 3b. Interestingly, compounds 7 and 8, which closely mimic the amide framework, were inactive. Additionally, compound 9 had low activity. Docking poses of compounds 7 and 8 suggest that reduced flexibly, resulting from the cyclization, may keep them from fitting into the hydrophobic pocket (FIG. 7). Similarly, additional methyl group in 9 may reduce the flexibility of the compound by introducing steric repulsion with the chlorine atom on ring B.

Although flexibility around amide linkage appears to be required for activity, it was not known if the carbonyl oxygen/carbonyl bond was needed to retain activity. Accordingly, reduced analogues of 3a and 3b, compounds 10 and 11, respectively were prepared, as shown Scheme 3. Design and synthesis of reduced amide benzene sulfonamide analogues.

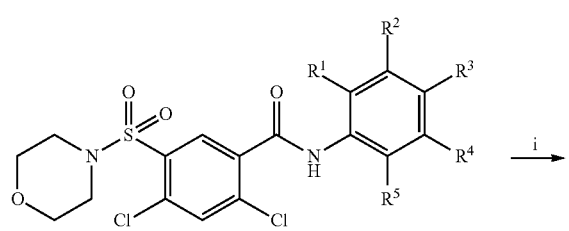

3a, $R^2 = R^3 = F, R^1 = R^4 = R^5 = H$
3b, $R^2 = R^3 = R^4 = F, R^1 = R^5 = H$

-continued

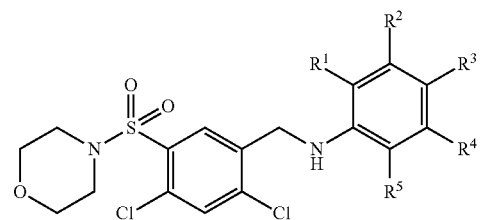

10, $R^2 = R^3 = F, R^1 = R^4 = R^5 = H$ (75%)
11, $R^2 = R^3 = R^4 = F, R^1 = R^5 = H$ (72%)

i. BH₃—DMS, THF (Sol), reflux 24 hrs. to 72 hrs.

The desired amines, 10 and 11, were obtained in good yields by straightforward reductions of 3a and 3b. Both of the compounds were subjected to ATX inhibition analysis to find that the 3,4,5-trifluoro amine, 11, inhibitory activity, although dramatically reduced relative to 3b (IC₅₀=395 nM versus 9 nM), remains in a respectable range as listed in Table 3. However, the activity of di-fluoro amine, 10, greatly deteriorated as shown in Table 3.

TABLE 3

Structure-activity data for the amines obtained from reduction of amide

| Compounds | IC$_{50}$ (nM ± SD) vs FS-3 | pNP-TMP Inhibition | Mechanism | logp | Molecular Weight |
|---|---|---|---|---|---|
| 10 | >1,000 | None | ND | 3.92 | 437.29 |
| 11 | 395.89 ± 44.12 | None | ND | 3.98 | 455.28 |

Figure 8:
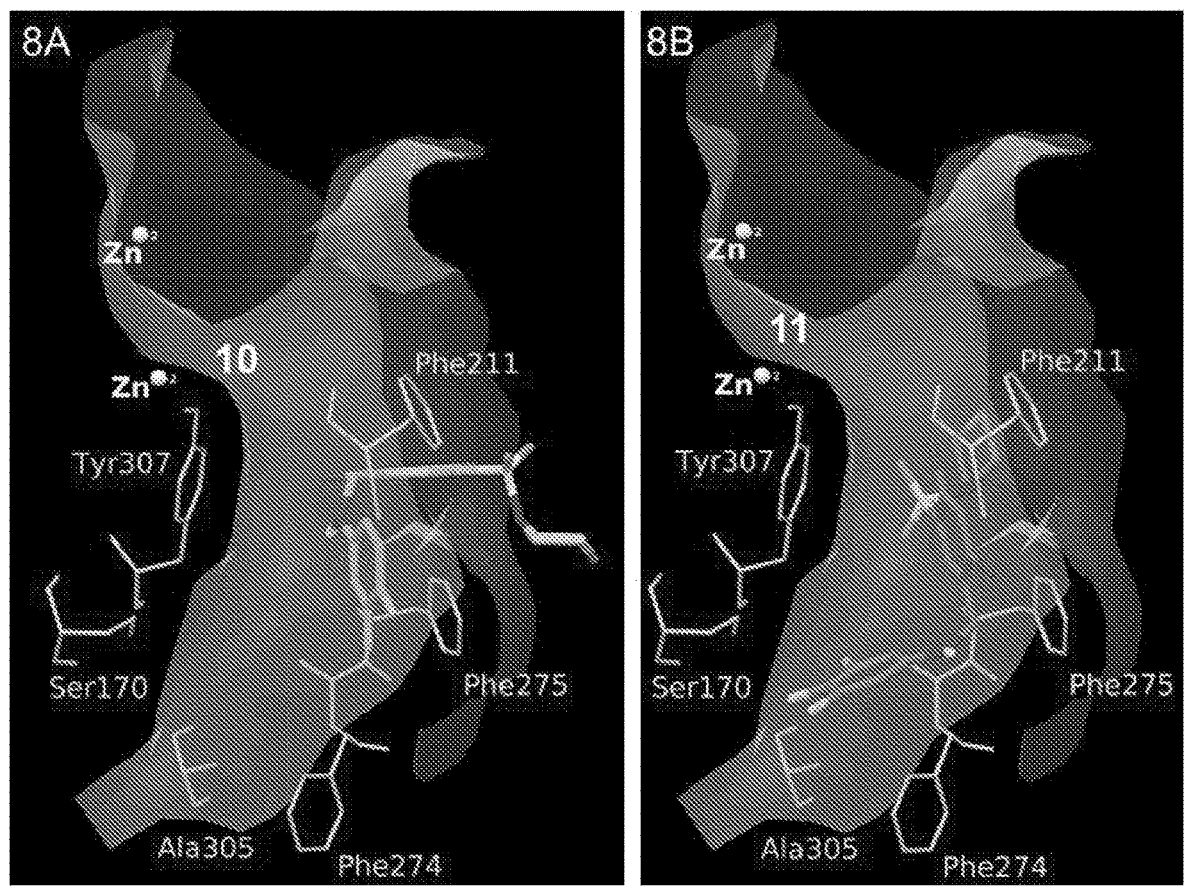
FIG. 8 depicts the binding pose of amines 10 and 11 in the ATX crystal structure (PDB 2XRG).
Figure 9:
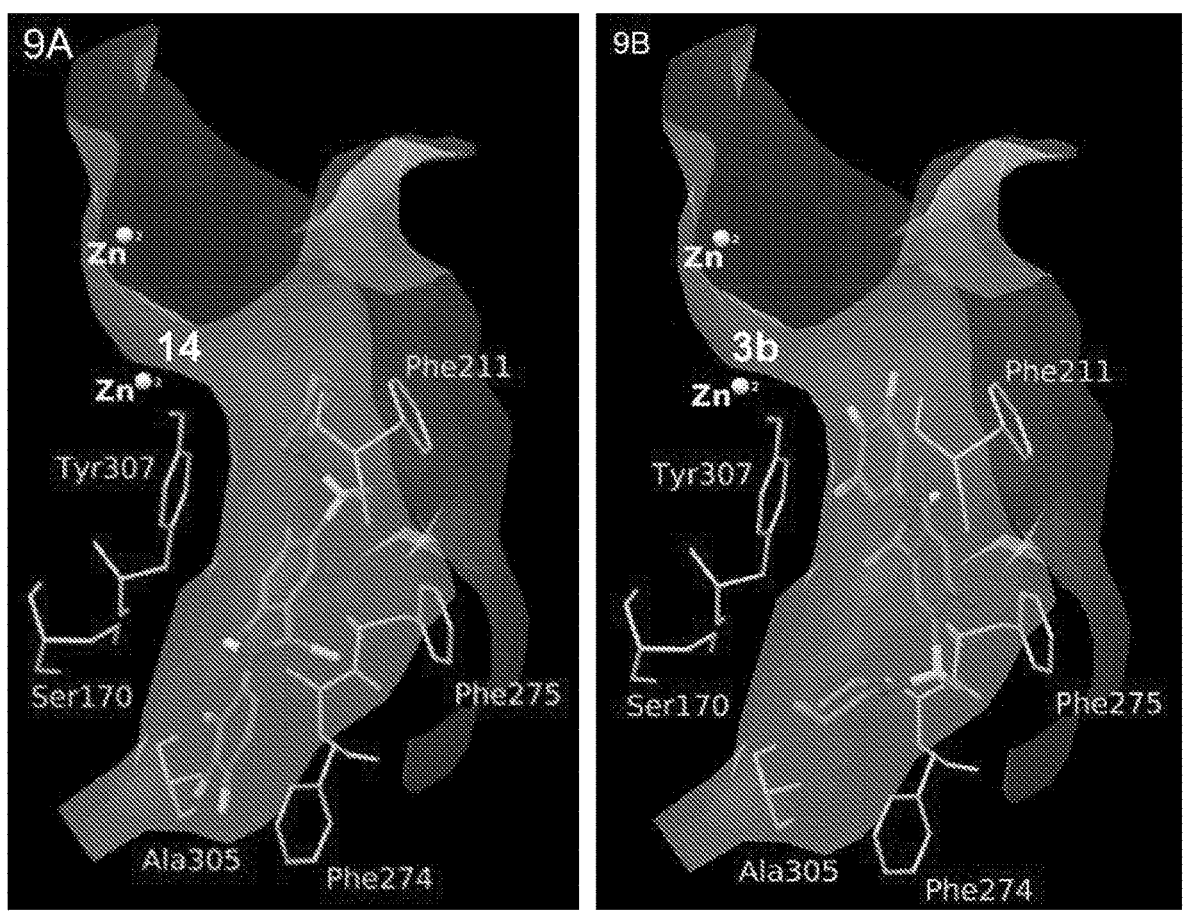
FIG. 9 depicts the binding poses of 14 (purple on left) and 3b (purple on right) in the ATX crystal structure (PDB 2XRG).
Figure 10:
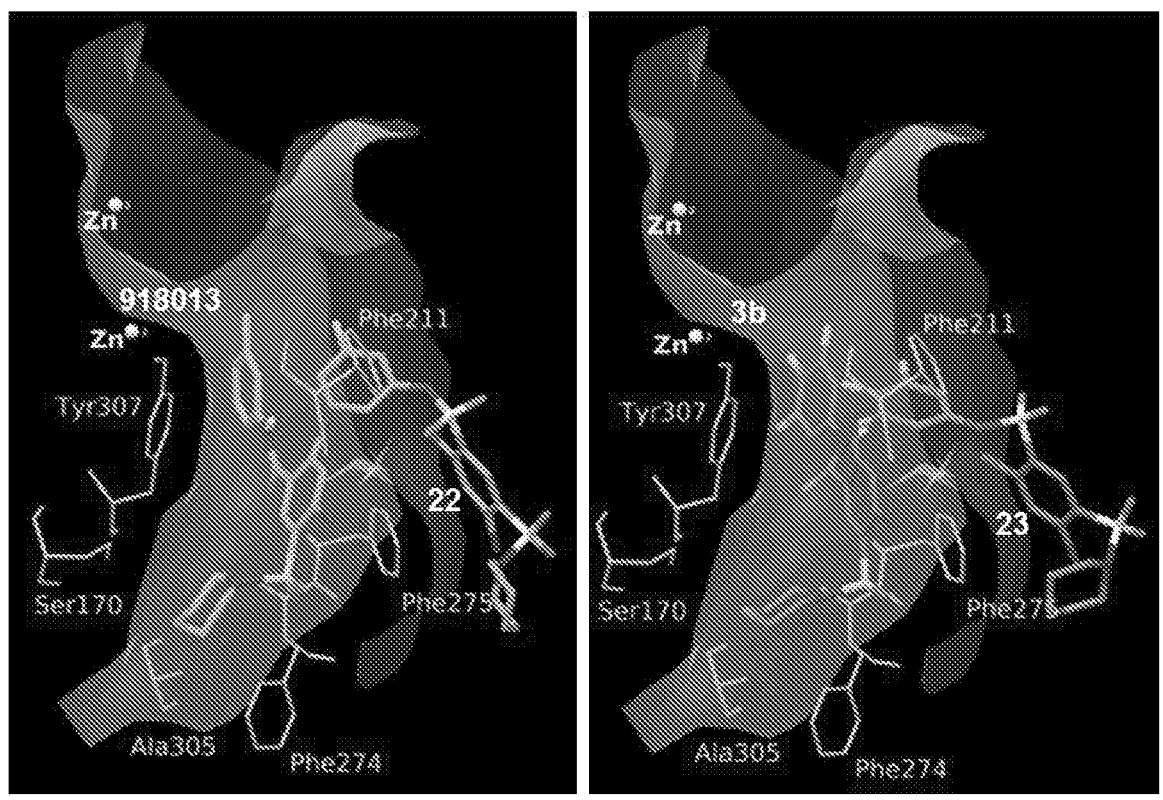
FIG. 10 depicts the binding pose of di-sulfonamides 22 (brown on left) and 23 (purple on right) in the ATX crystal structure (PDB 2XRG).

The docking poses of 10 and 11 suggest that compound 10 fits better into the hydrophobic pocket with ring A sticking deep into the hydrophobic pocket (FIG. 8). Next, given that thioamides are more stable against proteases than amides, thioamide analogs of the four most potent inhibitors were prepared utilizing the synthetic approach shown in Scheme4.[22] The thioamide compounds were tested for ATX inhibition and were found to retain the inhibitory activity in the close range in comparison to the amide analogues as shown in Table 4. The docking pose of 14 indicates that the compound fits into the hydrophobic pocket with inverted orientation in comparison to 3b (FIG. 9).

Scheme 4. Design and synthesis of thioamide benzene sulfonamide analogues.

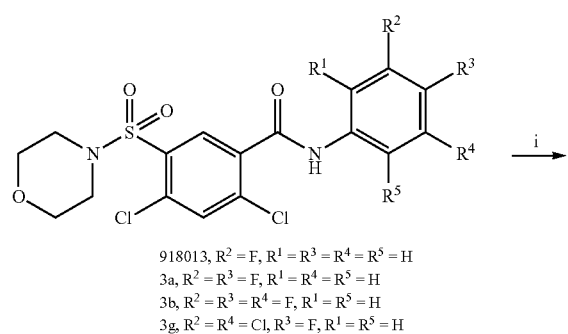

918013, $R^2$ = F, $R^1$ = $R^3$ = $R^4$ = $R^5$ = H
3a, $R^2$ = $R^3$ = F, $R^1$ = $R^4$ = $R^5$ = H
3b, $R^2$ = $R^3$ = $R^4$ = F, $R^1$ = $R^5$ = H
3g, $R^2$ = $R^4$ = Cl, $R^3$ = F, $R^1$ = $R^5$ = H

-continued

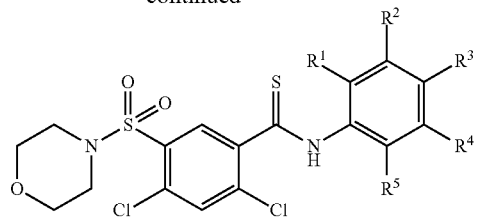

12, $R^2$ = F, $R^1$ = $R^3$ = $R^4$ = $R^5$ = H (68%)
13, $R^2$ = $R^3$ = F, $R^1$ = $R^4$ = $R^5$ = H (70%)
14, $R^2$ = $R^3$ = $R^4$ = F, $R^1$ = $R^5$ = H (71%)
15, $R^2$ = $R^4$ = Cl, $R^3$ = F, $R^1$ = $R^5$ = H (72%)

i. Lawesson's reagent, toluene (sol), Reflux

TABLE 4

Structure-activity data for thioamides

| Compounds | $IC_{50}$ (nM ± SD) vs FS-3 | pNP-TMP Inhibition | Mechanism | logp | Molecular Weight |
|---|---|---|---|---|---|
| 12 | 121.48 ± 1.02 | None | ND | 3.57 | 449.35 |
| 13 | 67.29 ± 9.73 | None | ND | 3.72 | 467.34 |
| 14 | 35.33 ± 2.66 | None | ND | 3.87 | 485.33 |
| 15 | 83.13 ± 9.77 | None | ND | 4.95 | 518.24 |

Next, the amide bond was substituted with sulfonamide, Scheme 5. The sulfonamide analogues were prepared through intermediate 18 as shown in scheme 5. Upon producing intermediate 18 in good yield, 18 was converted into two different kinds of sulfonamide. Compounds 19 and 20 have the sulfonamide nitrogen linked to the B-ring, and compounds 22 and 23 with the sulfonamide nitrogen linked to the A-ring. All four compounds were tested for the ATX inhibitory activity. However, the sulfonamide modification resulted in inactive compounds, Table 5, possible indicating a high sensitivity of ATX to the linker geometry.

Scheme 5. Design and synthesis of di-sulfonamide analogues

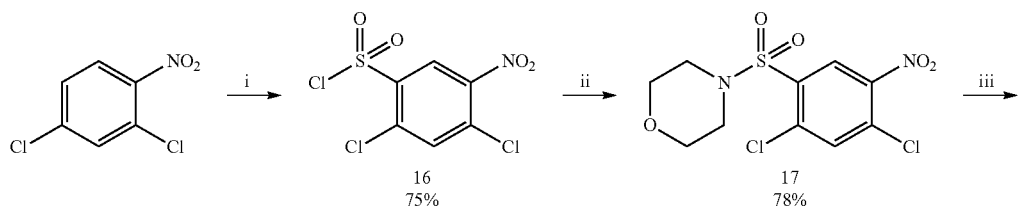

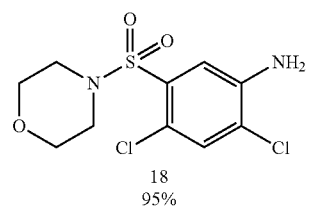

18
95%

-continued

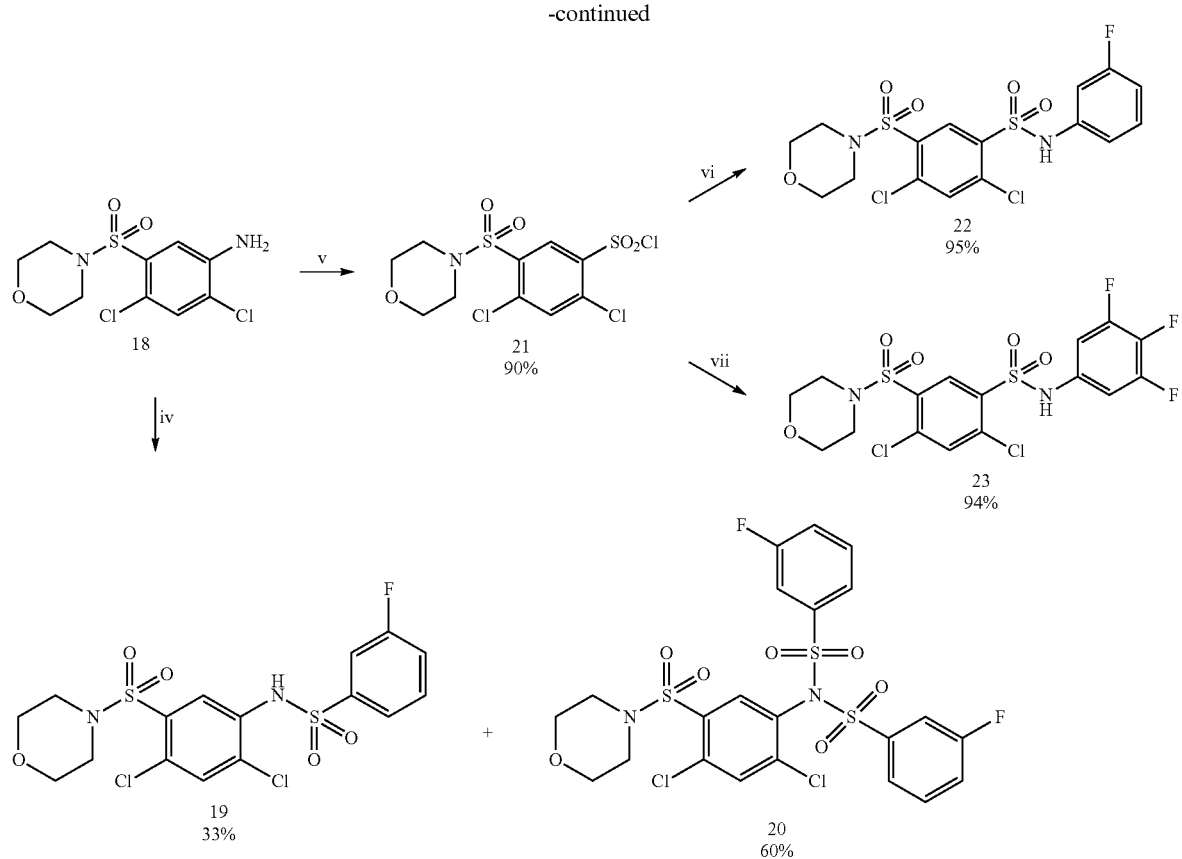

i. ClSO₃H, reflux, 12 hrs. ii. morpholine, Et₃N, R.T. 12 hrs. iii. iron powder, HCl, reflux, 5 hrs. iv. substituted-benzenesulfonyl chloride, Et₃N, DMAP, 96 hrs. v. NaNO₂, HCl, 0° C., SO₂, CH₃CO₂H. vi. 3-fluoroaniline, Et₃N. vii. 3,4,5-trifluoro aniline, Et₃N.

TABLE 5

Structure-activity data for the multi-sulfonamides

| Compounds | IC$_{50}$ (nM ± SD) vs FS-3 | pNP-TMP Inhibition | Mechanism | logp | Molecular Weight |
|---|---|---|---|---|---|
| 19 | >1,000 | None | ND | 1.92 | 469.33 |
| 20 | >1,000 | None | ND | 2.65 | 627.48 |
| 22 | >1,000 | None | ND | 1.91 | 469.33 |
| 23 | >1,000 | None | ND | 2.06 | 505.32 |

The docking poses of 22 and 23 suggest that, unlike 908013, these compounds are not located in the hydrophobic pocket. The inactivity of di-sulfonamide analogues could may be attributable to their three dimensional orientation.

These results indicate the importance of the amide linkage for inhibitory activity. Next, variations of the sulfonamide linkage between the B and C rings were explored in order to assess the importance of sulfonyl group. First, the sulfonamide linkage was replaced with a polar, but smaller, linkage, keeping the morpholine ring intact, as shown in Scheme 6.

Scheme 6. Design and synthesis of hydrazine analogues

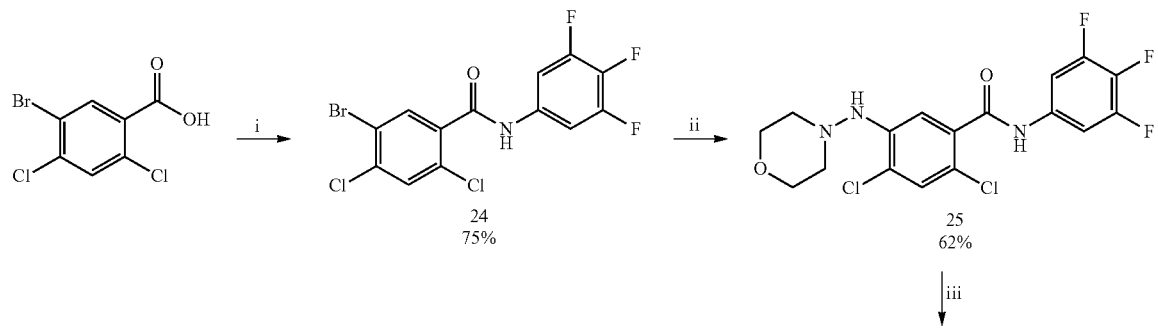

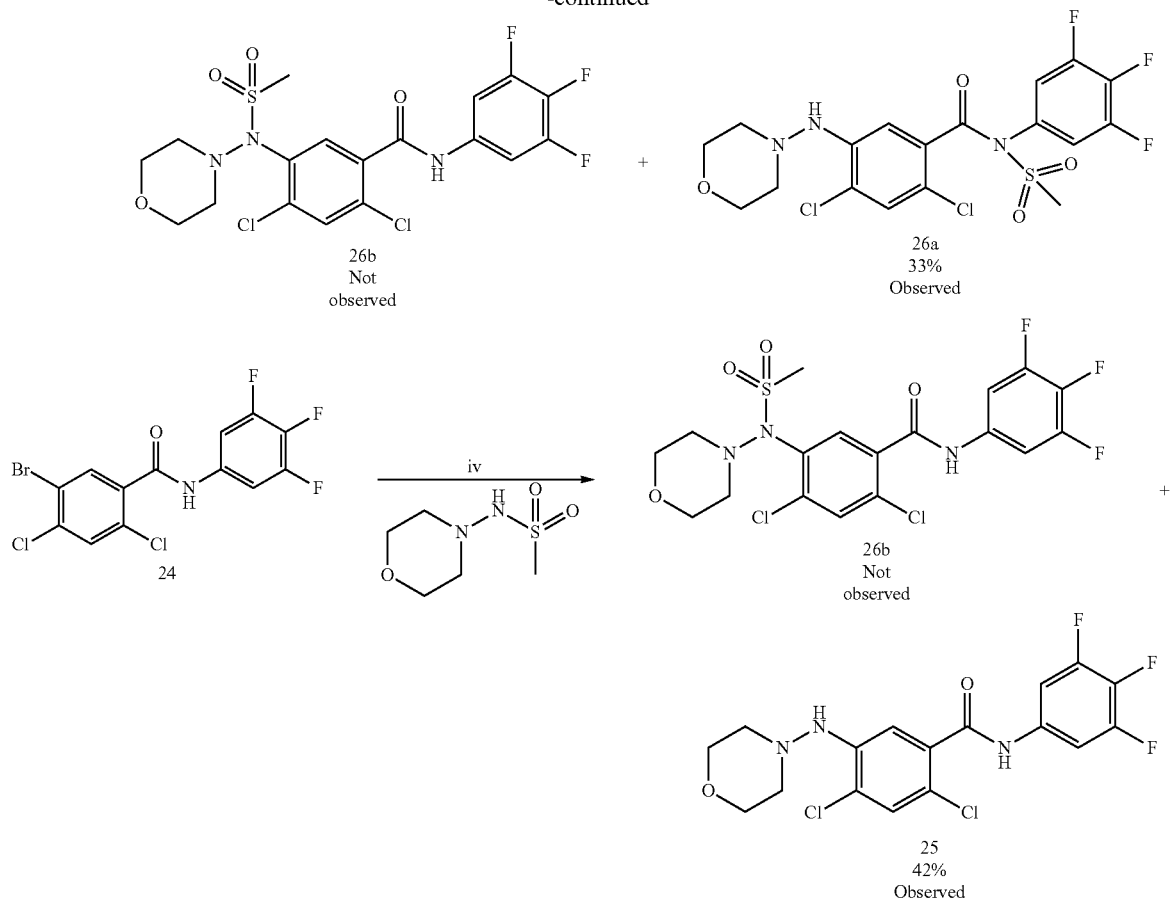

i. a) SOCl₂, DMF(cat), 12 hrs. R.T. b) 3,4,5-trifluoro-aniline, pyridine, 12 hrs. R.T. ii. 4-aminomorpholine, LiCl, Pd₂(dba)₃, Xantphos, NaOBu-t, 12 hrs. reflux.
iii. NaOBu-t, methanesulfonylchloride, 24 hrs. R.T. iv. N-morpholinomethanesulfonamide, [Pd(ally)Cl]₂, t-BuXphos, K₂CO₃

Compound 25 was obtained through intermediate 24 utilizing a Buchwald-Hartwig cross coupling reaction following the synthetic tools as demonstrated by Cacchi et al.[27] Compound 25 was tested for the ATX inhibitory activity and was found to be inactive (Table 6). This finding confirmed that sulfonyl linkage may better contact the polar receptor surface and form some electrostatic interactions to help the molecule strongly bind to the receptor as predicted by the molecular modelling in FIG. 4. Next, compound 25 was mesylated in an effort to obtain the sulfonamide 26b. 26b was thought to possibly be as effective as 3b in contacting the polar receptor surface. However, many attempts to obtain 26b following literature reported procedures were unsuccessful.[28-30] In one of the attempts utilizing excess sodium tert-butoxide and 1.1 equivalents of methane sulfonyl chloride, 26a was obtained. The compound 26a was also found to be inactive, once again indicating the importance of linker geometry.

Figure 11:
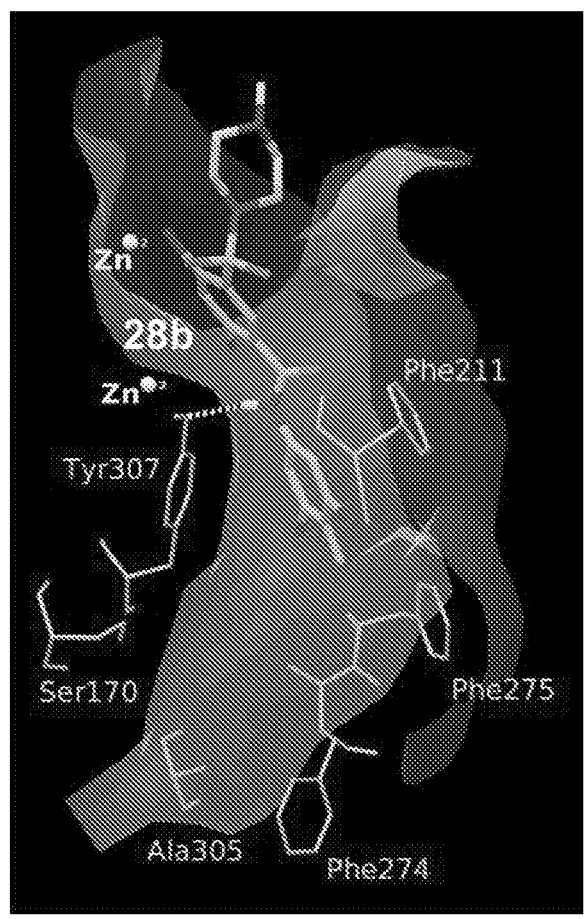
FIG. 11 depicts the binding pose of 28b in the ATX crystal structure (PDB 2XRG).

Finally, ring C was replaced with N-methyl-piperazine as shown in Scheme 7. It was reasoned that the piperazine analogues, if tolerated, would be more water soluble and more beneficial than morpholine analogues. The two most potent morpholine analogues, 3b and 3g, were selected and their N-methyl piperazine analogues, 28a and 28b, were prepared following the synthetic strategy shown in Scheme 7. Both of the piperazine analogues, 28a and 28b, were tested for ATX inhibition and found to inhibit the ATX in respectable range of 66 nM and 55 nM respectively as shown in Table 7. The more potent analogue, 28b, was turned into the corresponding thioamide 29. The thioamide, 29, was found to exhibit similar potency, 100 nM, as shown in Table 7. The docking pose of 28b suggests that the sulfonyl linkage reaches close to the catalytic site (FIG. 11). Additionally, the amide linkage may form a hydrogen bonding interaction with the Tyr 307. The ring A is placed into the hydrophobic pocket.

TABLE 6

Structure-activity data for hydrazine analogues

| Compounds | IC₅₀ (nM ± SD) vs FS-3 | pNP-TMP Inhibition | Mechanism | logp | Molecular Weight |
|---|---|---|---|---|---|
| 25 | >1,000 | None | ND | 3.49 | 420.21 |
| 26a | >1,000 | None | ND | 2.83 | 498.30 |

Scheme 7. Design and synthesis of piperazine analogues

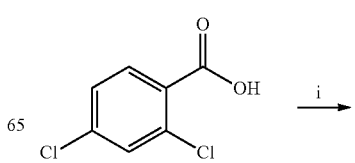

29
-continued

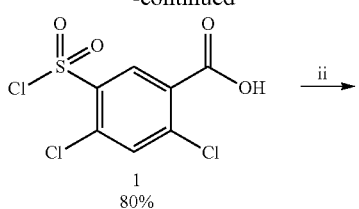

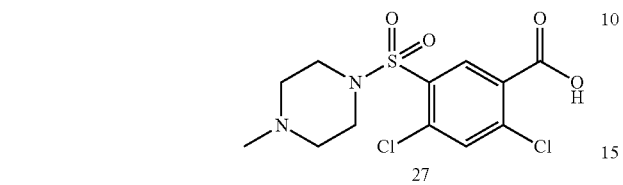

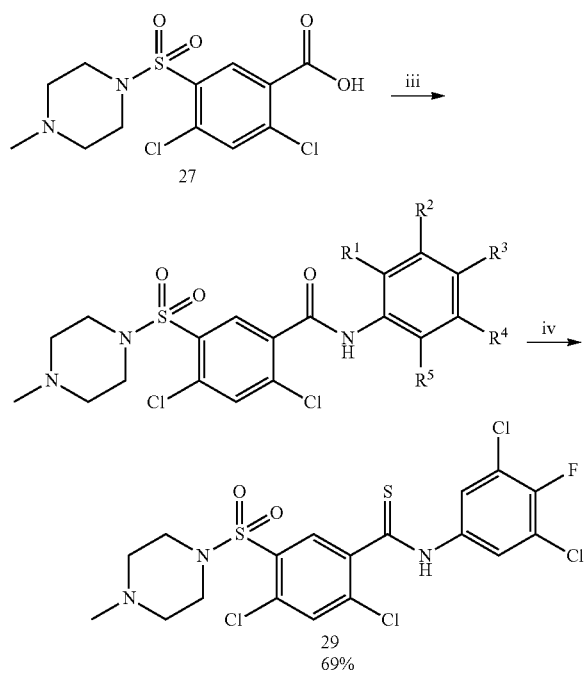

28a, $R^2 = R^3 = R^4 = F, R^1 = R^5 = H$ (65%)
28b, $R^2 = R^4 = Cl, R^3 = F, R^1 = R^5 = H$ (64%)

i. ClSO$_3$H, 12 hrs. reflux, ii. N-methylpiperazine, Et$_3$N, R.T. 12 hrs. iii. a) SOCl$_2$, DMF (cat), 12 hrs. R.T. (b) substituted-aniline, pyridine, 12 hrs. R.T. iv) Lawesson's reagent

30

TABLE 6

Structure-activity data for piperazine analogues

| Compounds | IC$_{50}$ (nM ± SD) vs FS-3 | pNP-TMP Inhibition | Mechanism | logp | Molecular Weight |
|---|---|---|---|---|---|
| 28a | 66.92 ± 7.15 | None | ND | 3.23 | 482.30 |
| 28b | 55.51 ± 8.81 | None | ND | 3.53 | 515.21 |
| 29 | 100.40 ± 8.11 | None | ND | 4.38 | 531.28 |

Example 2: Biological Results

Inhibition of ATX by Benzene Sulfonamide Series.

Compound 3b was found to be the most potent ATX inhibitor with an IC$_{50}$ of about 9 nM. The mechanism of action was determined to be competitive; however the traditional measure of a competitive inhibitor may not be appropriately applied in this context. 3b inhibited hydrolysis of the lipid-like substrate FS-3 while sparing effects on hydrolysis of the nucleotide substrate pNP-TMP. As such—and with the observed molecular modeling—it is known that 3b does not bind at the active site, in which case both substrates would be affected. However, because the compound is targeted toward the hydrophobic pocket of ATX, it shares space with the binding site for the hydrophobic tail of lipid substrates like FS-3. As such, the mechanism of action presents itself as "competitive" in the FS-3 hydrolysis assay even though the binding site of the 3b exists outside the catalytic site of the enzyme.

Selective Dose Dependent Inhibition of LPA1 Receptor by 3b, 3f and 3g.

Figure 12:
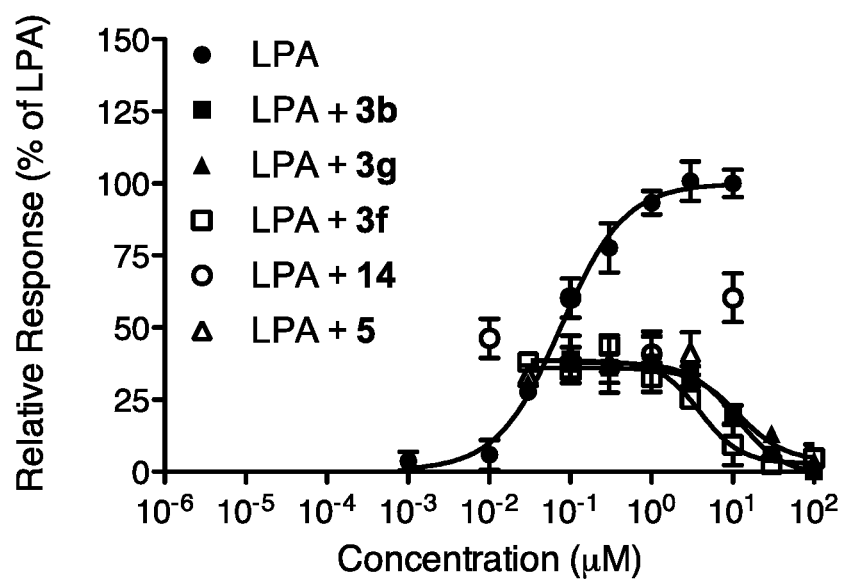
FIG. 12 depicts $Ca^{2+}$ Mobilization in LPA1 RH7777 cells.

None of the compounds tested exhibited agonist activity at any of the LPA receptor subtypes. Additionally, of those screened, only 3b, 3f, and 3g exhibited antagonist activity, and this was selectively at the LPA1 receptor (Table 7, FIG. 12). As such, 3b (ATX IC$_{50}$=9 nM, LPA1 IC$_{50}$=11 µM), 3f (ATX IC$_{50}$=83 nM, LPA1 IC$_{50}$=3.96 µM), and 3g (ATX IC$_{50}$=40 nM, LPA1 IC$_{50}$=11.86 µM), are the first dual inhibitors of both ATX and the LPA1 receptor.

TABLE 7

LPA-mediated Ca$^{2+}$ Mobilization

| | LPA1 RH7777 | | LPA2 MEF | | LPA3 RH7777 | | LPA4 CHO | | LPA5 B103 | |
|---|---|---|---|---|---|---|---|---|---|---|
| | EC$_{50}$ or IC$_{50}$ (µM) | E$_{max}$ (% LPA) | EC$_{50}$ or IC$_{50}$ (µM) | E$_{max}$ (% LPA) | EC$_{50}$ or IC$_{50}$ (µM) | E$_{max}$ (% LPA) | EC$_{50}$ or IC$_{50}$ (µM) | E$_{max}$ (% LPA) | EC$_{50}$ or IC$_{50}$ (µM) | E$_{max}$ (% LPA) |
| LPA1 18:1 | 0.08 ± 0.00 | 100.00 | 0.003 ± 0.00 | 100.00 | 0.29 ± 0.01 | 100.00 | 0.57 ± 0.01 | 100.00 | 0.14 ± 0.00 | 100.00 |
| LPA + 3b | 9.10 ± 1.2 | 37.99 | — | — | — | — | — | — | — | — |
| LPA + 3f | 3.96 ± 0.74 | 38.58 | ND | ND | ND | ND | ND | ND | ND | ND |
| LPA + 3g | 11.86 ± 1.12 | 36.08 | ND | ND | ND | ND | ND | ND | ND | ND |
| LPA + 14 | — | — | — | — | — | — | — | — | — | — |
| LPA + 5 | — | — | — | — | — | — | — | — | — | — |

Inhibition of ATX-Mediated Invasion in Vitro.

Figure 13:
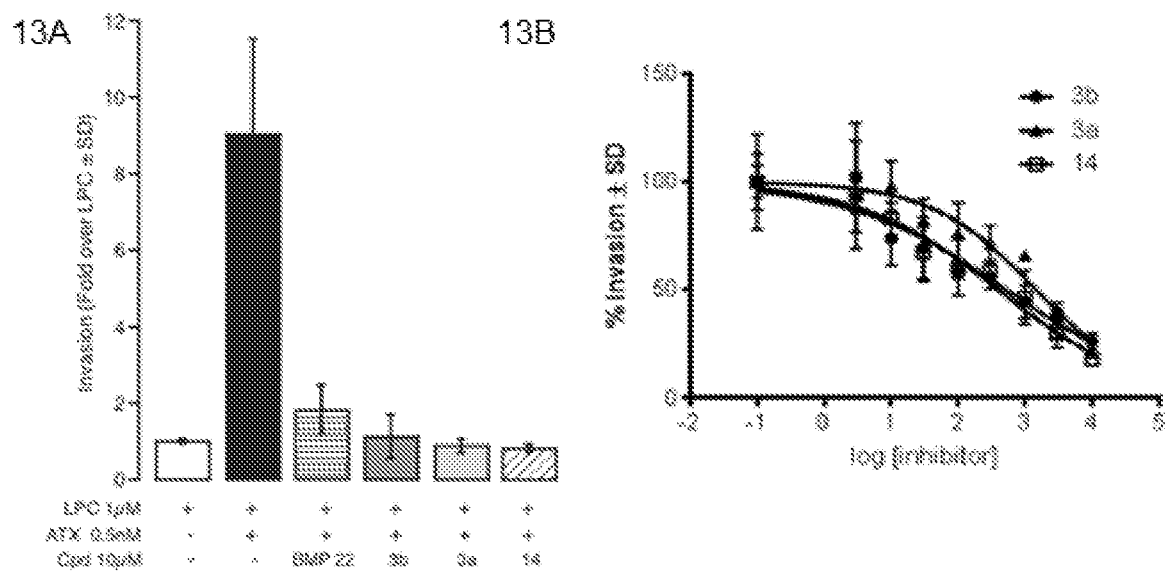
FIG. 13 (A) depicts the effect of the various ATX inhibitors on A2058 cell invasion. (B) depicts dose response curves generated in the presence of exogenous LPC, recombinant ATX and increasing concentrations of inhibitors as indicated.

The boyden chamber assay was used to assess the effect of three of the benzene sulfonamide analogues on cell invasion of A2058 human melanoma cells in vitro. The A2058 cells invade the matrigel layer in an LPA-dependent manner. Therefore, exogenous LPC and recombinant ATX was used as a source of LPA. Firstly, the compounds were screened at 10 μM concentration alongside BMP 22, a potent ATX inhibitor[31]. It was found that all the three inhibitors were as effective as BMP 22 in inhibiting A2058 cell invasion across the matrigel layer in response to exogenous LPC and recombinant ATX (FIG. 13A). Subsequently, dose response curves for compounds 3a, 3b and 14 were generated (FIG. 13B). All three inhibitors dose-dependently decreased the A2058 cell invasion with similar potencies (Table 8).

TABLE 8

$IC_{50}$ for compounds 3b, 3a, and 14 in cell invasion assay

| Compounds | $IC_{50}$ (nM) |
| --- | --- |
| 3b | 528 ± 13.94 |
| 3a | 1478 ± 12.29 |
| 14 | 403 ± 13.32 |

Conclusions

Provided herein are benzene-sulfonamide analogues that inhibit ATX with low nano-molar potency. The starting point for the synthetic optimization was the benzene-sulfonamide, 918013, a potent non-lipid ATX inhibitor identified through in silico search. In this study, four different kinds of structure activity explorations of 918013 were conducted. The structural features explored include a) modification of A-ring substituents, b) modification of amide bond A-B ring linker, c) modification of sulfonyl B-C ring linker, as well as d) the modification of C-ring. The A-ring optimization has resulted in a number of substantially more active ATX inhibitors, including thirteen fold more active inhibitor 3b as well as seven fold more active inhibitor 5 as shown in Scheme 8. In continuation, three of the potent inhibitors, 3b, 3f, and 3g, were very effective in selectively as well as dose dependently inhibiting $LPA_1$ expression. This is the first disclosure of potent ATX inhibitors, 3f ($IC_{50}$=83 nM) and 3b ($IC_{50}$=9 nM), antagonizing $LPA_1$ in such a low single digit micro-molar potency, 3f ($IC_{50}$=3.96 μM) and 3b ($IC_{50}$=9 μM).

Scheme 8. Potent compounds from A-ring optimization.

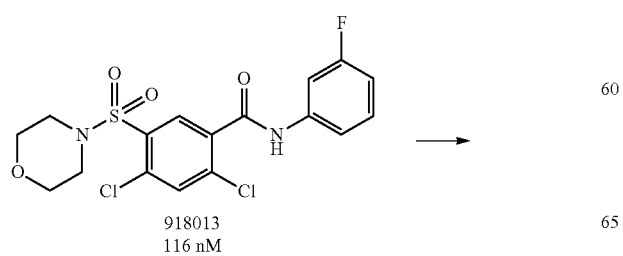

918013
116 nM

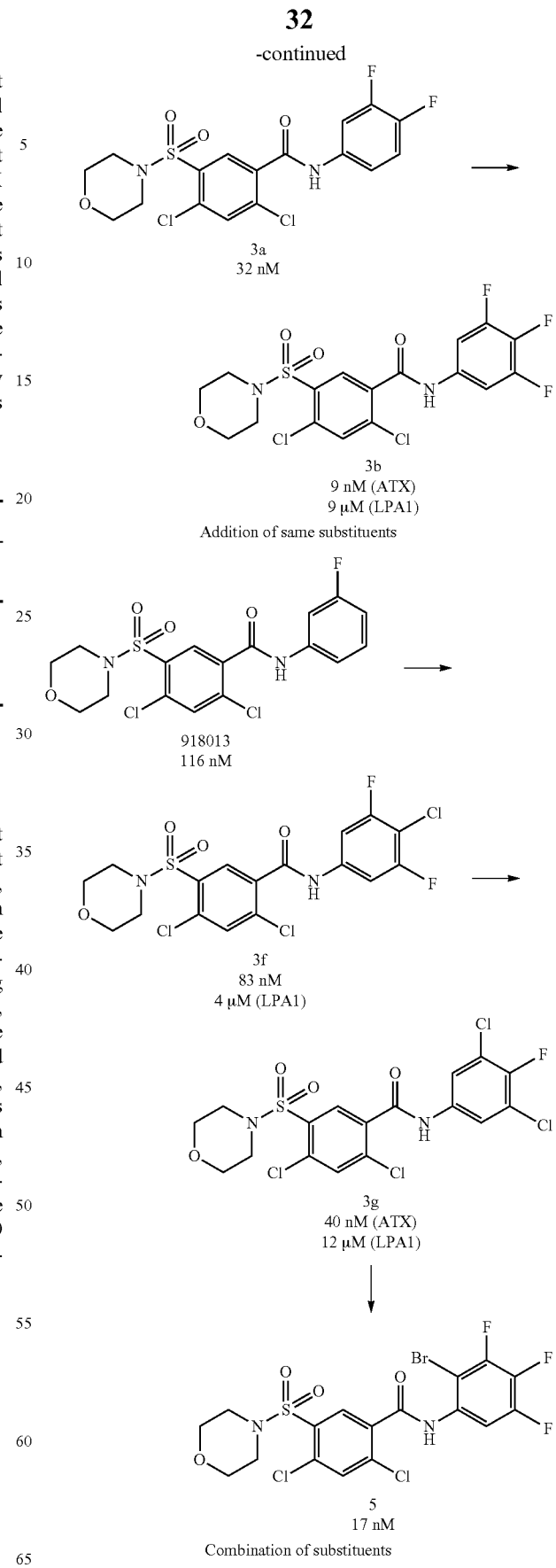

3a
32 nM 3b
9 nM (ATX)
9 μM (LPA1)
Addition of same substituents 918013
116 nM 3f
83 nM
4 μM (LPA1)

3g
40 nM (ATX)
12 μM (LPA1)

5
17 nM
Combination of substituents

The medicinal chemistry transformations of amide linkage were found to be highly sensitive for the ATX activity and, thus, any alterations led to deterioration in the activity. Thioamides, including compound 14 ($IC_{50}$=35 nM) were the most potent in this series, with three fold better potency than the screening hit. This finding provides insight into the importance of linker geometry in this series in order to bind to the ATX receptor. The third optimization, which is modification of sulfonyl linkage, did not result in any more active compounds in comparison to the screening hit 918013. This finding is in concert with the molecular modelling predictions suggesting the importance of a bigger polar linkage in contacting the polar surface of the receptor (FIG. 4). Finally, the last modification, replacement of morpholine with piperazine, was tolerated resulting in three more active compounds, including the most potent 28b ($IC_{50}$=55 nM) in this group. It is noteworthy that the piperazine series are soluble in water. In continuation, two most potent amide analogues (3a and 3b) as well as the most potent thioamide analogue (14) were picked to assess the effect of three of the benzene sulfonamide analogues on cell invasion of A2058 human melanoma cells in vitro. All three inhibitors have been observed to dose-dependently decrease the A2058 cell invasion with similar potencies (table 8). These results indicate that the benzene sulfonamide analogues were highly effective in reducing LPA-dependent invasion of A2058 human melanoma cells.

Example 3: Synthesis Experimentals

General methods: All non-aqueous reactions were performed in oven-dried glassware under an inert atmosphere of dry nitrogen. All the reagents and solvents were purchased from Aldrich (St. Louis, Mo.), Alfa-Aesar (Ward Hill, Mass.), Combi-Blocks (San Diego, Calif.), Ark Pharm (Libertyville, Ill.) and used without further purification. Analytical thin-layer chromatography was performed on Silica Gel GHLF 10×20 cm Analtech TLC Uniplates (Analtech, Newark, Del.) and were visualized by fluorescence quenching under UV light. Biotage SP1 Flash Chromatography Purification System (Charlotte, N.C.) (Biotage SNAP Cartridge, silica, 50 g & 100 g) was used to purify the compounds. 1H NMR and 13C NMR spectra were recorded on a Varian Inova-500 spectrometer (500 MHz) (Agilent Technologies, Santa Clara, Calif.) or a Bruker Ascend 400 (400 MHz) (Billerica, Mass.) spectrometer. Chemical shifts are reported in ppm on the δ scale and referenced to the appropriate solvent peak. Mass spectra were collected on a Brucker ESQUIRE electrospray/ion trap instrument in the positive and negative modes. High resolution mass spectrometer (HRMS) data were acquired on a Waters Xevo G2-S QTOF (Milford, Mass.) system equipped with an Acquity I-class UPLC system.

Synthesis of 2,4-dichloro-5-(chlorosulfonyl)benzoic Acid (1)

To a cooled (0° C.) chlorosulfonic acid (10.4 mL, 157 mmol) 2,4-dichlorobenzoic acid (5 g, 26 mmol) was added portion wise. The reaction mixture was subsequently heated to 140° C. and continued to stir for 16 hrs. The reaction mixture was cooled to room temperature and poured into crushed ice. The formed white precipitates were collected by filtration and dried under the vacuum. Yield=80%. The characterizations comply with the literature.[32]

General Procedure for the Synthesis of Compounds 2 and 27.

To a solution of 1 (3 g, 10.3 mmol) in 20 mL $CH_2Cl_2$, trimethylamine was added (3.61 mL, 26 mmol). The reaction mixture was cooled down to 0° C. under the ice. The corresponding secondary amine (11.4 mmol) was added drop-wise and the reaction mixture was continued to stir over the night. The reaction mixture was concentrated and the crude was taken for next step without further purification.

General Procedure for the Synthesis of Compounds 918013 as Well as 3a to 3i.

To a solution of compound 2 (0.46 g, 1.4 mmol) in 20 mL of $CH_2Cl_2$, a volume of 1 mL $SOCl_2$ (13.6 mmol) and 2 drops of DMF were added under argon atmosphere. The reaction was continued to stir at room temperature over the night. The reaction mixture was concentrated and dissolved back again in 20 mL $CH_2Cl_2$. Pyridine (330 uL, 4.1 mmol) and the corresponding aniline (1.2 mmol) were added under argon atmosphere. The reaction mixture was allowed to stir over the night at room temperature. The reaction mixture was extracted with 10% HCl, water, and brine solution. The organic layer was dried over $MgSO_4$, concentrated, and purified by column chromatography leading to the pure product.

2,4-dichloro-N-(3-fluorophenyl)-5-(morpholinosulfonyl)benzamide (918013)

The compound 908013 was prepared following general procedure for the synthesis of 908013 as well as 3a-3i. The crude was purified in 1% $MeOH/CH_2Cl_2$ yielding the pure product as white solid. Yield=70%. $^1$H NMR (400 MHz, DMSO-$d_6$) δ 10.94 (s, 1H), 8.18 (d, J=3.8 Hz, 2H), 7.77-7.67 (m, 1H), 7.53-7.37 (m, 2H), 7.12-6.95 (m, 1H), 3.69 (t, J=4.70 Hz, 4H), 3.28 (t, J=5.0 Hz, 4H). HRMS [$C_{17}H_{16}N_2O_4FSCl_2^+$]: calcd 433.0192, found 433.0182.

2,4-dichloro-N-(3,4-difluorophenyl)-5-(morpholinosulfonyl)benzamide (3a)

The compound 3a was prepared following general procedure for the synthesis of 908013 as well as 3a-3i. The crude was purified in 1% $MeOH/CH_2Cl_2$ yielding the pure product as white solid. Yield=72%. MP=221.3° C. $^1$H NMR (400 MHz, DMSO) δ 10.90 (s, 1H), 8.13 (s, 2H), 7.85 (ddd, J=12.8, 7.4, 2.4 Hz, 1H), 7.45 (ddd, J=27.0, 18.1, 9.0 Hz, 2H), 3.63 (t, J=4.46, 4H), 3.22 (t, J=4.77, 4H). $^{13}$C NMR (101 MHz, DMSO) δ 162.71, 135.72, 135.29, 134.19, 133.20, 133.10, 131.49, 117.76, 117.58, 116.22, 109.00, 108.79, 65.72, 45.49. HRMS [$C_{17}H_{15}N_2O_4F_2SCl_2^+$]: calcd 451.0098, found 451.0099.

2,4-dichloro-5-(morpholinosulfonyl)-N-(3,4,5-trifluorophenyl)benzamide (3b)

The compound 3b was prepared following general procedure for the synthesis of 908013 as well as 3a-3i. The crude was purified in 1% $MeOH/CH_2Cl_2$ yielding the pure product as white solid. Yield=71.5%. MP=237.8° C. $^1$H NMR (400 MHz, DMSO) δ 11.05 (s, 1H), 8.15 (d, J=2.1 Hz, 2H), 7.58 (dd, J=9.9, 6.5 Hz, 2H), 3.63 (t, J=4.67, 4H), 3.22 (t, J=4.53, 4H). 13C NMR (101 MHz, DMSO) δ 162.99, 135.70, 134.94, 134.27, 133.42, 133.17, 131.53, 104.39, 104.15, 65.72, 45.49. HRMS [$C_{17}H_{14}N_2O_4F_3SCl_2^+$]: calcd 469.0003, found 451.0012.

2,4-dichloro-5-(morpholinosulfonyl)-N-(perfluorophenyl)benzamide (3c)

The compound 3c was prepared following general procedure for the synthesis of 908013 as well as 3a-3i. The crude was purified in 1% MeOH/CH$_2$Cl$_2$ yielding the pure product as white solid. Yield=65%. MP=237.1° C. $^1$H NMR (400 MHz, DMSO-d$_6$) δ 11.01 (s, 1H), 8.15 (dd, J=24.5, 19.0 Hz, 2H), 3.70-3.55 (m, 4H), 3.27-3.13 (m, 4H). $^{13}$C NMR (101 MHz, DMSO-d$_6$) δ 166.95, 163.05, 136.00, 134.33, 133.82, 133.46, 131.49, 65.73, 45.43. HRMS [C$_{17}$H$_{12}$N$_2$4FSCl$_2$$^+$]: calcd 504.9815, found 504.9838.

2,4-dichloro-5-(morpholinosulfonyl)-N-(3,4,5-trichlorophenyl)benzamide (3d)

The compound 3d was prepared following general procedure for the synthesis of 908013 as well as 3a-3i. The crude was purified in 1% MeOH/CH$_2$Cl$_2$ yielding the pure product as white solid. Yield=75%. MP=303.0° C. $^1$H NMR (400 MHz, DMSO-d$_6$) δ 11.09 (s, 1H), 8.18 (s, 1H), 8.15 (s, 1H), 7.94 (s, 2H), 3.68-3.57 (t, J=4.32, 4H), 3.27-3.16 (t, J=4.84, 4H). $^{13}$C NMR (101 MHz, DMSO-d$_6$) δ 163.10, 138.36, 135.74, 134.78, 134.30, 133.52, 133.20, 133.01, 131.59, 124.51, 119.89, 65.72, 45.48. HRMS [C$_{17}$H$_{14}$N$_2$O$_4$SCl$_5$$^+$]: calcd 516.9117, found 516.9108.

2,4-dichloro-5-(morpholinosulfonyl)-N-(3,4,5-trimethoxyphenyl)benzamide (3e)

The compound 3e was prepared following general procedure for the synthesis of 908013 as well as 3a-3i. The crude was purified in 1% MeOH/CH$_2$Cl$_2$ yielding the pure product as white solid. Yield=65%. MP=281.2° C. $^1$H NMR (400 MHz, Chloroform-d) δ 8.34 (s, 1H), 7.83 (s, 1H), 7.66 (s, 1H), 6.93 (s, 2H), 3.89 (s, 6H), 3.84 (s, 3H), 3.73 (dd, J=5.9, 3.7 Hz, 4H), 3.39-3.18 (m, 4H). HRMS [C$_{20}$H$_{23}$N$_2$O$_7$SCl$_2$$^+$]: calcd 505.0603, found 505.0606.

2,4-dichloro-N-(4-chloro-3,5-difluorophenyl)-5-(morpholinosulfonyl)benzamide (3f)

The compound 3f was prepared following general procedure for the synthesis of 908013 as well as 3a-3i. The crude was purified in 1% MeOH/CH$_2$Cl$_2$ yielding the pure product as white solid. Yield=75%. MP=275.7° C. $^1$H NMR (400 MHz, DMSO-d$_6$) δ 11.17 (s, 1H), 8.16 (d, J=6.1 Hz, 2H), 7.60 (d, J=9.1 Hz, 2H), 3.63 (t, J=4.35, 4H), 3.22 (t, J=4.93, 4H). $^{13}$C NMR (101 MHz, CDCl$_3$) δ 168.38, 140.96, 140.08, 139.55, 138.75, 138.43, 136.82, 109.16, 108.89, 70.97, 50.74. HRMS [C$_{17}$H$_{14}$N$_2$O$_4$F$_2$SCl$_3$$^+$]: calcd 484.9708, found 484.9729.

2,4-dichloro-N-(3,5-dichloro-4-fluorophenyl)-5-(morpholinosulfonyl)benzamide (3g)

The compound 3g was prepared following general procedure for the synthesis of 908013 as well as 3a-3i. The crude was purified in 1% MeOH/CH$_2$Cl$_2$ yielding the pure product as white solid. Yield=76%. MP=297.4° C. $^1$H NMR (400 MHz, DMSO-d$_6$) δ 11.00 (s, 1H), 8.16 (d, J=9.9 Hz, 2H), 7.85 (d, J=6.1 Hz, 2H), 3.63 (t, J=4.8 Hz, 4H), 3.22 (t, J=5.22 Hz, 4H). $^{13}$C NMR (101 MHz, DMSO-d$_6$) δ 162.96, 135.74, 134.89, 134.28, 133.45, 133.18, 131.56, 121.11, 120.93, 120.19, 65.72, 45.49. HRMS [C$_{17}$H$_{14}$N$_2$O$_4$FSCl$_4$$^+$]: calcd 500.9412, found 500.9409.

2,4-dichloro-N-(4-cyano-3,5-difluorophenyl)-5-(morpholinosulfonyl)benzamide (3h)

The compound 3h was prepared following general procedure for the synthesis of 908013 as well as 3a-3i. The crude was purified in 1% MeOH/CH$_2$Cl$_2$ yielding the pure product as white solid. Yield=72%. MP=240.7° C. $^1$H NMR (400 MHz, DMSO) δ 11.51 (s, 1H), 8.19 (d, J=17.4 Hz, 2H), 7.63 (d, J=10.1 Hz, 2H), 3.63 (t, J=4.75 Hz, 4H), 3.22 (t, J=4.68, 4H). $^{13}$C NMR (101 MHz, DMSO-d$_6$) δ 163.67, 135.69, 134.51, 134.36, 133.73, 133.23, 131.69, 109.75, 103.18, 102.93, 65.72, 45.48. HRMS [C$_{18}$H$_{14}$N$_3$O$_4$F$_2$SCl$_2$$^+$]: calcd 476.0050, found 476.0048.

Methyl 4-(2,4-dichloro-5-(morpholinosulfonyl)benzamido)-2,6-difluorobenzoate (3i)

The compound 3i was prepared following general procedure for the synthesis of 908013 as well as 3a-3i. The crude was purified in 1% MeOH/CH$_2$Cl$_2$ yielding the pure product as white solid. Yield=69%. MP=216.4° C. $^1$H NMR (400 MHz, DMSO-d$_6$) δ 11.29 (s, 1H), 8.17 (d, J=14.8 Hz, 2H), 7.50 (d, J=10.6 Hz, 2H), 3.87 (s, 3H), 3.63 (t, J=4.46 Hz, 4H), 3.23 (t, J=4.69 Hz, 4H). $^{13}$C NMR (101 MHz, DMSO-d$_6$) δ 163.37, 160.85, 143.00, 135.70, 134.69, 134.34, 133.61, 133.19, 131.63, 103.16, 102.90, 65.72, 52.70, 45.49. HRMS [C$_{19}$H$_{17}$N$_2$O$_6$F$_2$SCl$_2$$^+$]: calcd 509.0152, found 509.0146.

4-(2,4-dichloro-5-(morpholinosulfonyl)benzamido)-2,6-difluorobenzoic Acid (4)

An amount of 8.5 mg LiOH (0.35 mmol) was added to a solution of compound 3i (90 mg, 0.17 mmol) in 10 THF/MeOH (2:1) mixture. The reaction mixture was allowed to stir over the night at room temperature. The reaction mixture was diluted with water, acidified with 10% HCl (pH=4), extracted with ethyl acetate. The organic layer was dried over MgSO$_4$ and purified through flash chromatography (2% MeOH/CH$_2$Cl$_2$) leading to the pure product as white solid. Yield=62%. MP=256.2° C. $^1$H NMR (400 MHz, DMSO-d$_6$) δ 13.63 (s, 1H), 10.73 (s, 1H), 8.12 (s, 1H), 7.57 (s, 1H), 7.52 (d, J=10.4 Hz, 2H), 4.01 (s, 3H), 3.62 (t, J=4.66 Hz, 4H), 3.14 (t, J=4.51 Hz, 4H). $^{13}$C NMR (101 MHz, DMSO-d$_6$) δ 163.12, 161.79, 159.94, 135.47, 132.99, 126.54, 123.22, 116.17, 103.04, 102.74, 65.67, 57.40, 45.50. HRMS [C$_{19}$H$_{18}$N$_2$7F$_2$SCl$^+$]: calcd 491.0491, found 491.0500.

N-(2-bromo-3,4,5-trifluorophenyl)-2,4-dichloro-5-(morpholinosulfonyl)benzamide (5)

The compound 5 was prepared following general procedure for the synthesis of 908013 as well as 3a-3i. The crude was purified in 1% MeOH/CH$_2$Cl$_2$ yielding the pure product as white solid. Yield=76%. MP=196.1° C. $^1$H NMR (400 MHz, DMSO-d$_6$) δ 10.64 (s, 1H), 8.21 (s, 1H), 8.12 (s, 1H), 7.86 (m, 1H), 3.64 (t, J=4.7 Hz, 4H), 3.23 (t, J=4.7 Hz, 4H). $^{13}$C NMR (101 MHz, DMSO-d$_6$) δ 163.37, 135.82, 134.80, 134.02, 133.29, 133.07, 131.77, 111.61, 65.71, 45.46. HRMS [C$_{19}$H$_{17}$N$_2$O$_6$F$_2$SCl$_2$$^+$]: calcd 546.9109, found 546.9113.

2-(2,4-dichloro-5-(morpholinosulfonyl)phenyl)-7-fluorobenzo[d]oxazole (7)

To a solution of 0.28 g of compound 2 (0.82 mmol) in 20 mL of CH2Cl2, was added a volume of 0.6 mL SOCl$_2$ (8.2 mmol) and catalytic amount of DMF (2 drops) under argon atmosphere. The reaction was allowed to sir for 12 hrs. The reaction mixture was concentrated and dissolved back in 20 mL CH2Cl2. A volume of 0.2 mL pyridine (2.5 mmol) as well as an amount of 0.105 g (0.82 mmol) 2-amino-6-fluorophenol was added to the solution under argon atmosphere. The reaction mixture was allowed to stir over the night at room temperature. The reaction mixture was diluted with 20 mL CH2Cl2 and extracted with 10% HCl. The organic layer was dried over MgSO4 and concentrated. The crude was dissolved in 25 mL toluene. An amount of 156 mg p-TSA (0.82 mmol) was added to the solution under argon atmosphere. The reaction mixture was refluxed over 12 hrs. The reaction was cooled down to room temperature, poured into water and extracted with ethyl acetate. The organic layer was separated then washed with water, brine, dried (MgSO$_4$), filtered and concentrated. The crude product was purified by column chromatography (silica gel, 30% ethyl acetate/hexanes) to afford the desired product as an off-white solid. Yield=77%. MP=167.4° C. $^1$H NMR (400 MHz, Chloroform-d) δ 8.87 (s, 1H), 7.80 (s, 1H), 7.66 (dd, J=8.0, 0.9 Hz, 1H), 7.37 (td, J=8.2, 4.6 Hz, 1H), 7.21 (ddd, J=9.9, 8.3, 0.9 Hz, 1H), 3.90-3.62 (m, 4H), 3.49-3.20 (m, 4H). $^{13}$C NMR (101 MHz, CDCl$_3$) δ 158.89, 148.30, 145.78, 144.63, 138.44, 137.84, 135.44, 134.80, 125.61, 124.72, 116.62 (d, J=4.3 Hz), 113.09, 112.93, 66.51, 45.90. HRMS [C$_{17}$H$_{14}$N$_2$O$_4$FSCl$_2$$^+$]: calcd 431.0035, found 431.0045.

4-((2,4-dichloro-5-(5,6-difluoro-1H-benzo[d]imidazol-2-yl)phenyl)sulfonyl)-morpholine (8)

To a solution of 0.28 g of compound 2 (0.82 mmol) in 20 mL of CH$_2$Cl$_2$, was added a volume of 0.6 mL SOCl$_2$ (8.2 mmol) and catalytic amount of DMF (2 drops) under argon atmosphere. The reaction was allowed to sir for 12 hrs. The reaction mixture was concentrated and dissolved back in 20 mL CH$_2$Cl$_2$. A volume of 0.2 mL pyridine (2.5 mmol) as well as an amount of 0.118 g (0.82 mmol) 4, 5-difluorobenzene-1,2-diamine was added to the solution under argon atmosphere. The reaction mixture was allowed to stir over the night at room temperature. The mixture was diluted with dichloromethane (30 ml) and washed with saturated aqueous sodium bicarbonate solution (80 ml). The organic phase was dried over MgSO$_4$ and the solvent removed to provide the amide as a mixture of isomers. The crude amide was combined with phosphorus oxychloride (10 ml) under an argon atmosphere, heated to reflux for 100 minutes, then allowed to cool down to room temperature. The mixture was poured into ice-water (100 ml) and neutralized with 2N sodium hydroxide solution. Saturated aqueous sodium bicarbonate solution (60 ml) was added and the aqueous phase was extracted with ethyl acetate (3×70 ml). Water (150 ml) was added to the combined organic phases and the pH was adjusted to 3 with 2N aqueous hydrochloric acid. The organic layer was washed with brine (100 ml), dried over MgSO$_4$ and the solvent removed to give a brown solid. The crude was purified by flash chromatography (35% EtOAc/hexanes) to afford the desired product as light brown solid. Yield=71%. MP=175.2° C. $^1$H NMR (400 MHz, DMSO-d$_6$) δ 8.51 (s, 1H), 8.19 (s, 1H), 7.83-7.71 (m, 2H), 3.64 (t, J=4.8 Hz, 5H), 3.24 (dd, J=5.9, 3.6 Hz, 4H). $^{13}$C NMR (101 MHz, DMSO-d$_6$) δ 148.55, 148.41, 146.18, 136.45, 134.30, 134.20, 133.91, 132.88, 128.32, 65.71, 54.87, 45.48. HRMS [C$_{17}$H$_{14}$N$_3$O$_3$F$_2$SCl$_2$$^+$]: calcd 448.0101, found 448.0106.

2,4-dichloro-N-(3-fluorophenyl)-N-methyl-5-(morpholinosulfonyl)benzamide (9)

The compound 9 was prepared following general procedure for the synthesis of 908013 as well as 3a-3i. The crude was purified in 1% MeOH/CH$_2$Cl$_2$ yielding the pure product as white solid. Yield=75%. MP=128.7° C. $^1$H NMR (400 MHz, DMSO-d$_6$) δ 8.16-7.72 (m, 2H), 7.47-7.24 (m, 2H), 7.22-6.99 (m, 2H), 3.57 (t, J=4.6 Hz, 4H), 3.40 (s, 3H), 2.95 (bt, J=5.2 Hz, 4H). $^{13}$C NMR (101 MHz, DMSO-d$_6$) δ 164.16, 160.61, 144.17, 135.50, 135.09, 133.32, 133.03, 132.68, 132.05, 131.84, 130.86, 123.31, 114.57, 65.53, 45.47, 36.60. HRMS [C$_{18}$H$_{18}$N$_2$O$_4$FSCl$_2$$^+$]: calcd 447.0348, found 447.0369.

N-(2,4-dichloro-5-(morpholinosulfonyl)benzyl)-3,4-difluoroaniline (10)

To a solution of compound 3a (0.15 g, 0.33 mmol) in anhydrous THF (20 mL), a volume of 47 µL of BH$_3$.DMS (0.5 mmol) was added under argon atmosphere. The reaction mixture was allowed to reflux over 72 hrs and reaction progress was monitored by TLC. The reaction was quenched with 30 mL of water, extracted with ethyl acetate. The organic layer was extracted with brine and dried over MgSO$_4$. The crude was purified through flash chromatography (silica gel, 40% EtOAc/hexanes) providing access to the pure product as white solid. Yield=75%. MP=154.8° C. $^1$H NMR (400 MHz, CDCl$_3$) δ 7.89 (s, 1H), 7.53 (s, 1H), 6.96-6.79 (m, 1H), 6.33-6.10 (m, 2H), 4.35 (d, J=6.0 Hz, 2H), 4.23 (t, J=5.9 Hz, 1H), 3.58 (t, J=4.44 Hz, 4H), 3.03 (t, J=4.54 Hz, 4H). $^{13}$C NMR (101 MHz, DMSO-d$_6$) δ 145.36, 137.86, 136.88, 133.19, 132.53, 131.01, 130.11, 117.66, 117.48, 108.10, 100.73, 100.53, 65.50, 45.45, 43.83. HRMS [C$_{17}$H$_{17}$N$_2$O$_3$F$_2$SCl$_2$$^+$]: calcd 437.0305, found 437.0307.

N-(2,4-dichloro-5-(morpholinosulfonyl)benzyl)-3,4,5-trifluoroaniline (11)

To a solution of compound 3b (0.15 g, 0.32 mmol) in anhydrous THF (20 mL), a volume of 46 µL of BH$_3$.DMS (0.48 mmol) was added under argon atmosphere. The reaction mixture was allowed to reflux over 24 hrs and reaction progress was monitored by TLC. The reaction was quenched with 30 mL of water, extracted with ethyl acetate. The organic layer was extracted with brine and dried over MgSO$_4$. The crude was purified through flash chromatography (silica gel, 40% EtOAc/hexanes) providing access to the pure product as white solid. Yield=72%. MP=149.4° C. $^1$H NMR (400 MHz, CDCl$_3$) δ 7.89 (s, 1H), 7.54 (s, 1H), 6.16-5.94 (m, 2H), 4.31 (dd, J=13.5, 5.0 Hz, 3H), 3.61 (t, J=4.84 Hz, 4H), 3.08 (t, J=5.0 Hz, 4H). 13C NMR (101 MHz, DMSO) δ 152.26, 149.91, 144.61, 137.99, 136.42, 133.27, 132.60, 131.01, 130.33, 96.08, 95.84, 65.54, 45.47, 43.66. HRMS [C$_{17}$H$_{16}$N$_2$O3F$_3$SCl$_2$$^+$]: calcd 455.0211, found 455.0206.

General Procedure for the Synthesis of Compounds from 12-15.

To a solution of 0.2 g (1 equivalent) 908013, 3a, 3b, or 3g in toluene (20 mL), was Lawesson's reagent (0.9 equivalent) under argon atmosphere as demonstrated in the literature.[22] The reaction was allowed to reflux over 12 hrs. The reaction was cooled down to room temperature. The solvent was evaporated and the crude was purified through flash chromatography (silica gel, 30%-35% EtOAc/hexanes) yielding the pure product as the light yellow solid.

2,4-dichloro-N-(3-fluorophenyl)-5-(morpholinosulfonyl)benzothioamide (12)

The compound 12 was obtained following the general procedure for the preparation of compounds 12-15. The crude was purified through flash column (silica gel, 30% EtOAc/hexanes) leading to the pure product as the light yellow solid. Yield=68%. MP=181.0° C. $^1$H NMR (400 MHz, DMSO-d$_6$) δ 12.45 (s, 1H), 8.11 (s, 1H), 8.06 (dt, J=11.4, 2.3 Hz, 1H), 8.00 (s, 1H), 7.71-7.64 (m, 1H), 7.53 (td, J=8.2, 6.7 Hz, 1H), 7.19 (td, J=8.5, 1.8 Hz, 1H), 3.65 (t, J=4.64 Hz, 4H), 3.21 (t, J=4.72 Hz, 4H). $^{13}$C NMR (101 MHz, DMSO-d$_6$) δ 141.97, 133.92, 133.71, 132.78, 131.68, 131.18, 130.68, 130.59, 118.73, 109.48, 109.23, 65.68, 45.51. HRMS [C$_{17}$H$_{16}$N$_2$O3FS$_2$Cl$_2$$^+$]: calcd 448.9963, found 448.9956.

2,4-dichloro-N-(3,4-difluorophenyl)-5-(morpholinosulfonyl)benzothioamide (13)

The compound 13 was obtained following the general procedure for the preparation of compounds 12-15. The crude was purified through flash column (silica gel, 32% EtOAc/hexanes) leading to the pure product as the light yellow solid. Yield=70%. $^1$H NMR (400 MHz, CDCl$_3$) δ 9.55 (s, 1H), 8.19-7.86 (m, 2H), 7.71-7.40 (m, 2H), 7.31-7.15 (m, 1H), 3.71 (bs, 4H), 3.23 (bs, 4H). $^{13}$C NMR (101 MHz, CDCl$_3$) δ 192.37, 151.23 (d, J=13.4 Hz), 150.07 (d, J=12.8 Hz), 148.76 (d, J=13.4 Hz), 147.58 (d, J=12.7 Hz), 141.70, 134.58, 134.44, 133.99, 133.39, 132.76, 132.39, 119.40 (d, J=2.4 Hz), 117.69, 117.50, 112.99, 112.78, 66.31, 45.87. HRMS [C$_{17}$H$_{15}$N$_2$O$_3$F$_2$S$_2$Cl$_2$$^+$]: calcd 466.9869, found 466.9869.

2,4-dichloro-5-(morpholinosulfonyl)-N-(3,4,5-trifluorophenyl)benzothioamide (14)

The compound 14 was obtained following the general procedure for the preparation of compounds 12-15. The crude was purified through flash column (silica gel, 35% EtOAc/hexanes) leading to the pure product as the light yellow solid. Yield=71%. MP=152.1° C. $^1$H NMR (400 MHz, CDCl$_3$) δ 9.41 (s, 1H), 8.05 (s, 1H), 7.68 (dd, J=8.7, 6.2 Hz, 2H), 7.59 (s, 1H), 3.73 (t, J=5.23 Hz, 4H), 3.25 (t, J=5.23 Hz, 4H). $^{13}$C NMR (101 MHz, CDCl$_3$) δ 191.63, 151.41, 140.50, 133.31, 133.21, 132.36, 132.08, 131.50, 106.82, 106.57, 65.33, 44.87. HRMS [C$_{17}$H$_{14}$N$_2$O$_3$F$_3$S$_2$Cl$_2$$^+$]: calcd 484.9775, found 484.9778.

2,4-dichloro-N-(3,5-dichloro-4-fluorophenyl)-5-(morpholinosulfonyl)-benzothioamide (15)

The compound 15 was obtained following the general procedure for the preparation of compounds 12-15. The crude was purified through flash column (silica gel, 35% EtOAc/hexanes) leading to the pure product as the light yellow solid. Yield=72%. MP=175.2° C. $^1$H NMR (400 MHz, DMSO-d$_6$) δ 12.51 (s, 1H), 8.17 (d, J=6.0 Hz, 2H), 8.11 (s, 1H), 8.05 (s, 1H), 3.65 (bt, J=4.41 Hz, 4H), 3.21 (bt, J=4.31 Hz, 4H). $^{13}$C NMR (101 MHz, DMSO-d$_6$) δ 192.75, 152.43, 149.96, 141.53, 135.81 (d, J=4.4 Hz), 134.01, 133.78, 132.83, 131.92, 131.20, 123.89, 121.07, 120.88, 65.68, 45.51. HRMS [C$_{17}$H$_{14}$N$_2$O$_3$FS$_2$Cl$_4$$^+$]: calcd 516.9184, found 516.9227.

2,4-dichloro-5-nitrobenzene-1-sulfonyl chloride (16)

Intermediate 16 was prepared following the experimental procedure for the preparation of intermediate 1 starting with 5 g of 2,4-dichloro-1-nitrobenzene (26 mmol). An amount of 5.7 g (19.6 mmol, 75%) pure product was obtained as off white solid upon drying under the vacuum. $^1$H NMR (400 MHz, DMSO-d$_6$) δ 8.44 (s, 1H), 7.91 (s, 1H).

4-((2,4-dichloro-5-nitrophenyl)sulfonyl)morpholine (17)

Intermediate 17 was prepared following the general procedure for the preparation of intermediate 2 and 27 staring with 3.5 g of intermediate 16 (12 mmol). An amount of 3.2 g (9.3 mmol, 78%) pure product was obtained as the off white solid. $^1$H NMR (400 MHz, CDCl$_3$) δ 8.61 (s, 1H), 7.79 (s, 1H), 3.75 (t, J=4.71 Hz, 4H), 3.35 (t, J=4.31 Hz, 4H).

2,4-dichloro-5-(morpholinosulfonyl)aniline (18)

The nitro intermediate 17 (3 g, 8.8 mmol) was dissolved in a mixture of EtOH and H$_2$O (40 mL, 10:1). Powdered iron (2.25 g, 35.2 mmol) and five drops of HCl (12 M) were added. The mixture was refluxed 5 hrs. The mixture was cooled to room temperature and the solvent was evaporated. HCl (1N, 100 mL) was added and the mixture was extracted with EtOAc (100 mL). The organic phase was extracted with brine, dried over MgSO4 and concentrated providing the pure product as the light red solid (2.6 g, 8.3 mmol, 95%). $^1$H NMR (400 MHz, DMSO-d$_6$) δ 7.58 (s, 1H), 7.41 (s, 1H), 6.04 (bs, 2H), 3.54 (t, J=5.0 Hz, 4H), 3.13 (t, J=4.86 Hz, 4H). Synthesis of Compound 19 and 20.

To a solution of 0.2 g 18 (0.64 mmol) in 15 mL CH$_2$Cl$_2$, was added Et$_3$N (267 μL, 1.9 mmol), 3-fluorobenzenesulfonyl chloride (0.149 g, 0.77 mmol), and catalytic amount of DMAP under argon atmosphere. The reaction was allowed to stir at room temperature over 96 hrs and monitored by TLC. Reaction led to formation of two new spots as determined by TLC. The reaction mixture was diluted with 30 mL CH$_2$Cl$_2$. Organic layer was extracted with 10% HCl, H$_2$O, brine, and evaporated under reduced pressure. The crude with two spots were isolated by flash chromatography (silica gel, 30%45% EtOAc/hexanes) providing pure compound 19 (yield=33%) and 20 (yield=60%) as white solids. Compound 19. $^1$H NMR (400 MHz, CDCl$_3$) δ 8.24 (s, 1H), 7.72-7.43 (m, 4H), 7.33 (tdd, J=8.3, 2.5, 0.9 Hz, 1H), 3.74 (t, J=5.10 Hz, 4H), 3.28 (t, J=5.04 Hz, 4H). $^{13}$C NMR (101 MHz, CDCl$_3$) δ 163.71, 161.19, 140.34 (d, J=6.8 Hz), 135.81, 132.61, 132.43, 131.42 (d, J=7.8 Hz), 129.09, 128.41, 123.97, 123.28 (d, J=3.4 Hz), 121.42, 121.21, 114.94, 114.70, 66.47, 45.93. HRMS [C$_{16}$H$_{16}$N$_2$O$_5$FS$_2$Cl$_2$$^+$]: calcd 468.9862, found 467.9870. Compound 20. $^1$H NMR (400 MHz, CDCl$_3$) δ 7.90-7.37 (m, 10H), 3.73 (t, J=4.86 Hz, 4H), 3.27 (t, J=4.69 Hz, 4H). [C$_{22}$H$_{19}$N$_2$O$_7$F$_2$S$_3$Cl$_2$$^+$]: calcd 626.9699, found 626.9702.

2,4-dichloro-5-(morpholinosulfonyl)benzene-1-sulfonyl chloride (21)

The intermediate 21 was prepared from 1.5 g (4.8 mmol) of intermediate 18 following the literature reported procedure.[33] An amount of 1.7 g intermediate 21 (4.3 mmol, 90%) was obtained as the off white solid upon drying the precipitate under the vacuum. The product was taken for the next step.

General Procedure for the Formation of Compound 22 and 23.

To a solution of 0.2 g 21 (0.51 mmol) in 15 mL of CH$_2$Cl$_2$, was added Et$_3$N 1.53 mmol) and appropriate aniline derivative (1.2 equivalent) under argon atmosphere. The reaction was allowed to stir at room temperature over 12 hrs. The reaction was diluted with 30 mL CH$_2$Cl$_2$, extracted with 10% HCl, H2O, and brine. The organic layer was dried over MgSO$_4$, concentrated under reduced pressure. The crude was purified through flash column (silica gel, 2% MeOH/CH$_2$Cl$_2$) yielding the pure product as off white solid.

2,4-dichloro-N-(3-fluorophenyl)-5-(morpholinosulfonyl)benzenesulfonamide (22)

Yield=95%. MP=170.7° C. $^1$H NMR (400 MHz, DMSO-d$_6$) δ 11.28 (s, 1H), 8.41 (s, 1H), 8.22 (s, 1H), 7.33 (dd, J=15.0, 8.2 Hz, 1H), 7.01-6.77 (m, 3H), 3.59 (t, J=4.23 Hz, 4H), 3.09 (t, J=4.64 Hz, 4H). $^{13}$C NMR (101 MHz, DMSO-d$_6$) δ 163.43, 161.0, 159.69, 138.36, 136.84, 136.21, 135.68, 135.42, 134.05, 133.34, 131.33, 131.24, 115.46, 111.25, 111.04, 106.59, 106.34, 65.60, 45.43. HRMS [C$_{16}$H$_{16}$N$_2$O$_5$FS$_2$Cl$_2$$^+$]: calcd 468.9861, found 468.9857.

2,4-dichloro-5-(morpholinosulfonyl)-N-(3,4,5-trifluorophenyl)benzenesulfonamide (23)

Yield=94%. MP=107.8° C. $^1$H NMR (400 MHz, Chloroform-d) δ 8.61 (s, 1H), 7.73 (s, 1H), 7.18 (bs, 1H), 6.90-6.70 (m, 2H), 3.76-3.65 (m, 4H), 3.31-3.17 (m, 4H). $^{13}$C NMR (101 MHz, DMSO-d$_6$) δ 151.57, 149.06, 137.15, 136.19, 135.81, 135.12, 134.30, 133.34, 104.62, 104.55, 104.38, 65.63, 45.42. HRMS [C$_{16}$H$_{14}$N$_2$O$_5$F$_3$S$_2$Cl$_2$$^+$]: calcd 504.9673, found 504.9679.

5-bromo-2,4-dichloro-N-(3,4,5-trifluorophenyl)benzamide (24)

Intermediate 24 was prepared following the synthetic technique for the preparation of 3a-3i starting with 2 g of 5-bromo-2,4-dichlorobenzoic acid (7.4 mmol). An amount of 2.22 g (5.6%, 75%) Pure 24 was obtained as a white solid upon purification through flash column (silica gel, 45% EtOAc/hexanes). $^1$H NMR (400 MHz, Chloroform-d) δ 8.15 (s, 1H), 7.58 (s, 1H), 3.92 (s, 3H).

2,4-dichloro-5-(morpholinoamino)-N-(3,4,5-trifluorophenyl)benzamide (25)

Compound 25 was prepared from compound 24 (0.3 g, 0.75 mmol) following the literature reported procedure of LiCl mediated palladium catalyzed coupling of hydrazine and phenyl bromide.$^{27}$ An amount of 0.195 g (0.46 mmol, 62%) pure product was obtained as light yellowish solid upon purification through flash column (silica gel, 30% EtOAC/hexanes). MP=196.1° C. $^1$H NMR (400 MHz, Chloroform-d) δ 7.95 (s, 1H), 7.65 (s, 1H), 7.51-7.29 (m, 3H), 5.15 (s, 1H), 3.81 (t, J=4.6 Hz, 4H), 2.78 (bt, 4H). $^1$H NMR (400 MHz, DMSO-d$_6$) δ 10.86 (s, 1H), 7.77-7.41 (m, 3H), 7.29 (s, 1H), 7.05 (s, 1H), 3.67 (t, J=4.4 Hz, 4H), 2.79 (t, J=4.7 Hz, 4H). $^{13}$C NMR (101 MHz, DMSO-d$_6$) δ 165.16, 151.31, 148.88, 142.82, 135.57, 129.64, 117.71, 116.95, 112.40, 103.99, 103.75, 66.28, 54.47. HRMS [C$_{17}$H$_{15}$N$_3$O$_2$F$_3$Cl$_2$$^+$]: calcd 420.0493, found 420.0484.

2,4-dichloro-N-(methylsulfonyl)-5-(morpholinoamino)-N-(3,4,5-trifluorophenyl)-benzamide (26a)

To a solution of 0.1 g of 25 (0.24 mmol) in DMSO, was added NaO$^t$Bu (0.069 g, 0.72 mmol) at 0° C. under argon atmosphere. Methanesulfonylchloride (22 μL, 0.29 mmol) was added and the reaction was allowed to stir over 24 hrs at ambient temperature. The reaction was diluted with water and extracted with EtOAc (30 mL). The organic layer was washed with water, brine, dried over MgSO$_4$, and concentrated under reduced pressure. The crude was purified through column chromatography leading to compound 26a (0.04 g, 0.08 mmol) as an off white solid. $^1$H NMR (400 MHz, CDCl$_3$) δ 7.18 (s, 1H), 7.12 (s, 1H), 6.99 (dd, J=7.4, 6.0 Hz, 2H), 5.06 (s, 1H), 3.84 (t, J=4.46 Hz, 4H), 3.58 (s, 3H), 2.68 (bt, 4H). $^{13}$C NMR (101 MHz, CDCl$_3$) δ 167.13, 142.04, 132.69, 130.52, 130.16, 120.12, 118.85, 115.26, 115.03, 112.93, 66.81, 56.42, 42.05. HRMS [C$_{18}$H$_{17}$N$_3$O$_4$F$_3$SCl$_2$$^+$]: calcd 498.0269, found 498.0263.

2,4-dichloro-5-((4-methylpiperazin-1-yl)sulfonyl)-N-(3,4,5-trifluorophenyl)-benzamide (28a)

Compound 28a was prepared from compound 27 (0.2 g, 0.57 mmol) and 3,4,5-trifluoro aniline following the synthetic technique for the preparation of 3a-3i. Pure compound 28a was obtained as white solid upon purification (silica gel, 10% MeOH/CH$_2$Cl$_2$). Yield=65%. MP=201.5° C. $^1$H NMR (400 MHz, DMSO-d$_6$) δ 11.04 (s, 1H), 8.14 (d, J=6.4 Hz, 2H), 7.58 (dd, J=9.9, 6.5 Hz, 2H), 3.24 (t, J=4.49 Hz, 4H), 2.36 (t, J=4.74 Hz, 4H), 2.18 (s, 3H). $^{13}$C NMR (101 MHz, DMSO-d$_6$) δ 163.01, 135.55, 134.90, 134.72, 133.32, 133.09, 131.42, 104.42, 104.17, 53.91, 45.24. HRMS [C$_{18}$H$_{17}$N$_3$O$_3$F$_3$SCl$_2$$^+$]: calcd 482.0320, found 482.0340.

2,4-dichloro-N-(3,5-dichloro-4-fluorophenyl)-5-((4-methylpiperazin-1-yl)sulfonyl)benzamide (28b)

Compound 28b was prepared from compound 27 (0.2 g, 0.57 mmol) and 3,5-dichloro-4-fluoro aniline following the synthetic technique for the preparation of 3a-3i. Pure compound 28b was obtained as white solid upon purification (silica gel, 10% MeOH/CH$_2$Cl$_2$). Yield=64%. MP=232.7° C. $^1$H NMR (400 MHz, DMSO) δ 11.00 (s, 1H), 8.15 (d, J=14.8 Hz, 2H), 7.85 (d, J=6.1 Hz, 2H), 3.23 (t, J=4.38 Hz, 4H), 2.35 (t, J=4.38 Hz, 4H), 2.18 (s, 3H). $^{13}$C NMR (101 MHz, DMSO-d$_6$) δ 162.98, 135.57, 134.86, 134.73, 133.33, 133.10, 131.45, 121.10, 120.92, 120.20, 53.94, 45.41, 45.35. HRMS [C$_{18}$H$_{17}$N$_3$O$_3$F$_3$SCl$_2$$^+$]: calcd 513.9729, found=513.9743.

2,4-dichloro-N-(3,5-dichloro-4-fluorophenyl)-5-((4-methylpiperazin-1-yl)sulfonyl)-benzothioamide (29)

Compound 29 was prepared from 28b following the synthetic procedure for the preparation of 12-15. Pure compound 29 was obtained as light purple solid upon purification (silica gel, 3% MeOH/CH$_2$Cl$_2$). Yield=69%. 1H NMR (400 MHz, CDCl$_3$) δ 9.60 (s, 1H), 8.04 (s, 1H), 7.94 (d, J=5.8 Hz, 2H), 7.57 (s, 1H), 3.30 (bm, 4H), 2.47 (bm, 4H), 2.31 (s, 3H). $^{13}$C NMR (101 MHz, DMSO) δ 141.62, 134.36, 133.63, 132.75, 131.74, 131.08, 123.93, 121.04, 120.85, 53.79, 45.18. HRMS [C$_{18}$H$_{17}$N$_3$O$_2$FS$_2$Cl$_4$$^+$]: calcd 529.9500, found=529.9503.

Example 4: Biological Procedures

Method:

ATX Generation: Human recombinant ATX was expressed as published previously, using Sf9 *Spodoptera frugiperda* ovary cells (Invitrogen, Carlsbad, Calif.).$^{13}$ Suspension cells were grown to a 1 liter quantity at a concentration of 1×10$^6$ cells/ml in Sf-900 III serum-free medium (Invitrogen) supplemented with 50 U/ml penicillin and 50 μg/ml streptomycin at 27° C. with agitation. Cells were then infected with high-titer baculovirus generated via Bac-to- Bac Baculovirus Expression System (Invitrogen) using the pCMV5 mammalian expression vector containing the C-terminal FLAG-tagged human ATX sequence (a generous gift from Dr. Junken Aoko, ohoku University, Aoba-ku, Sendai, Japan) subcloned into the pFastBacl transfer vector. Expression was allowed to proceed for 72 h, and secreted protein was harvested by centrifugation and filtration of the culture medium followed by affinity chromatography using anti-FLAG M2 agarose beads (Sigma-Aldrich, St. Louis, Mo.) and competitive elution with 50 µg/ml FLAG peptide (Sigma-Aldrich). Resultant ATX was then concentrated via centrifugation in Amicon Ultra 30,000 molecular weight cut off filter units (Millipore, Billerica, Mass.) and subsequent buffer exchange into storage buffer comprised of 50 mM Tris, pH 7.4 with 20% (v/v) ethylene glycol. Protein was held at −80° C. for long-term storage.

ATX Inhibition: ATX activity was assessed via hydrolysis of the synthetic, lipid-like FRET-based substrate FS-3 (Echelon Biosciences, Salt Lake City, Utah) or via hydrolysis of the nucleotide substrate p-nitrophenyl thymidine 5'-monophosphate (pNP-TMP) as described previously.[2] Reaction wells were loaded in 60 µl volumes in triplicate wells of half-area, black-wall 96-well plates in assay buffer consisting of 50 mM Tris, 140 mM NaCl, 5 mM KCl, 1 mM $CaCl_2$, 1 mM $MgCl_2$, 10 M BSA, pH 8.0. For dose-response and $IC_{50}$ generation, final concentrations per reaction well were comprised of 1 µM FS-3 (or 1 mM pNP-TMP), 0 or 4 nM human recombinant ATX and test compound concentrations ranging from 0 to 1 µM. To determine mechanism of action, triplicate wells were loaded in assay buffer with FS-3 concentrations ranging from 0 to 10 µM, 0 or 4 nM ATX and inhibitor concentrations of 0, $0.5 \times IC_{50}$ or $2 \times IC_{50}$. Fluorescence was read every 2 minutes for 1 hour at excitation/emission wavelengths of 485/528 nm for FS-3 hydrolysis or 405 nm absorbance for pNP-TMP hydrolysis using a FlexStation 3 microplate reader (Molecular Devices, Sunnyvale, Calif.). Data (relative fluorescence or absorbance) were then recorded as a mean value of the triplicates for each sample versus time. Percent ATX activity (±SD) were calculated from the 1 hour time point data for each inhibitor concentration, and GraphPad Prism version 5.0a (GraphPad Software, San Diego, Calif.) was then used to fit non-linear regression curves, fitting the Hill Slope from the data in a variable slope model and interpolating from the curve to determine the $IC_{50}$ (±SD) for each compound. In the case of mechanism determination, the linear fluorescence data from time 10 minutes to 30 minutes were then transformed using a carboxyfluorescein standard curve to determine product concentration and plotted separately. Linear trend lines were inserted using Microsoft Excel, the slope of which represent the rates of reaction for each substrate concentration. This reaction rate data for each inhibitor concentration were then plotted against substrate (FS-3) concentration and simultaneously fitted via non-linear regression in the Michaelis-Menten equations for competitive, non-competitive, uncompetitive, and mixed-mode inhibition using GraphPad Prism version 5.0a. Mechanism of inhibition was determined by which curve fit had the best global fit ($R^2$ value).

Selective Dose Dependent Inhibition of LPA1 Receptor by 3b, 3f and 3g.

Methods:

Cell Culture: LPA1 and LPA3 RH7777 rat hepatoma cells were generated in-house as described previously[34] and maintained in DMEM supplemented with 10% FBS and 2 mM L-glutamine with 250 µg/ml G418. LPA2 MEF mouse embryonic fibroblast cells were also derived from LPA1 and LPA2 double knockout mouse embryos as described previously[35] and maintained in DMEM supplemented with 10% FBS, 2 mM L-glutamine, 100 U/ml penicillin and 100 µg/ml streptomycin. LPA4 CHO chinese hamster ovary cells were a generous gift from Dr. Takao Shimizu (Tokyo University, Tokyo, Japan) and were maintained in Ham's F12 medium supplemented with 10% FBS, 2 mM L-glutamine and 350 µg/ml G418. LPA5 B103 rate neuroblastoma cells were derived in house via lentiviral transduction of FLAG-tagged LPA5 and puromycin selection as published[36] and maintained in DMEM supplemented with 10% FBS and 0.4 µg/ml puromycin. All cells were maintained at 37° C. with 5% $CO_2$ in a humidified atmosphere.

Calcium Mobilization: As published previously, LPAR activation leads to transient calcium mobilization. In order to assess receptor activation or antagonism, compounds were tested in stable transfectant cell lines engineered to overexpress a single LPAR subtype.[36] At the level of each receptor, calcium mobilization was assessed via fluorescence in Fura-2AM-loaded cells treated with a dose range of test compound both in the absence and presence of the $EC_{50}$ concentration of LPA 18:1 corresponding to the appropriate receptor subtype and cell line. All cells were plated in triplicate in 96-well, black-wall plates at a density of $5 \times 10^4$ cells per well and allowed to adhere overnight. LPA1 and LPA3 RH7777 cells were plated in poly-L-lysine coated plates. LPA5 B103 cells were plated in Matrigel-coated plates. After adherence, cells were serum-deprived in Krebs buffer consisting of 10 mM HEPES, pH 7.4 with 120 mM NaCl; 5 mM KCl; 1.8 mM $CaCl_2$; 0.62 mM $MgSO_4$; 6 mM D-glucose. LPA1 RH7777, LPA3 RH7777 and LPA5 B103 cells were serum-deprived for 4 hours, while LPA2 MEF cells were serum-deprived for 1 hour, and LPA4 CHO cells were not serum-deprived. Fura 2-AM was then loaded for 30 minutes at a concentration of 4.5 µg/ml in Krebs buffer with 0.45% (v/v) Pluronic F-127 (and additionally 0.1% BSA and 2.5 mM Probenicid for LPA4 CHO cells), after which cells were switched to fresh Krebs buffer. Finally, the robotics of a FlexStation 3 microplate reader were used to apply a dose-range of LPA 18:1 (in a 1:1 molecular complex with lipid-depleted BSA) or test compounds ranging from 0 to 100 µM in the presence and absence of the $EC_{50}$ concentration of LPA 18:1 for each LPA receptor subtype. Fluorescence corresponding to calcium mobilization was immediately monitored upon addition every 3.42 seconds over a span of 70 seconds total at excitation/emission wavelengths of 340/510 and 380/510 nm. Data (relative fluorescence) were then recorded as a mean fluorescence ratio value of the triplicates for each concentration and normalized to percentage of LPA 18:1 $E_{max}$. GraphPad Prism version 5.0a was then used to plot the data and fit non-linear regression curves in a variable slope model in order to determine the pharmacodynamics ($EC_{50}$ or $IC_{50}$) of the compounds in $Ca^{2+}$ mobilization.

In Vitro Invasion Assay.

Methods:

In vitro invasion assay—A2058 human melanoma cell line (gift from Dr. Timothy Clair, NCI, National Institutes of Health) was cultured in Dulbecco's modified Eagle's medium (DMEM) supplemented with 10% (V/V) FBS, 100 U/mL penicillin, 100 µg/mL streptomycin and 2 mM L-glutamine (Life Technologies). Cell invasion was performed using the 24-well BD Biocoat™ tumor invasion system (BD Biosciences, 8 µm-pore size). Briefly, the matrigel coating was rehydrated with PBS at 37° C. for 2 h. After removal of PBS, $5 \times 10^4$ A2058 cells in serum-free DMEM supplemented with 0.1% BSA were plated to each upper chamber. 0.75 ml of serum-free DMEM/0.1% BSA containing chemoattractant (recombinant ATX plus 1 µM of 18:1 LPC) with or without the respective ATX inhibitors was added to the bottom chamber. Cells were allowed to invade the matrigel for 20 h at 37° C. To stain the invaded cells, the media in the upper chamber was first removed and the insert was transferred to a new 24-well plate containing 4 µg/ml of calcien AM (Molecular Probes, Life Technologies) in Hank's balanced salt solution (HBSS) and incubated for 1 h at 37° C. The fluorescent invaded cells were measured using the FLEXstation II plate reader (Molecular Devices) at excitation and emission wavelengths of 485 and 530 nm, respectively.

CITATIONS (1) Schleicher, S. M.; Thotala, D. K.; Linkous, A. G.; Hu, R.; Leahy, K. M.; Yazlovitskaya, E. M.; Hallahan, D. E. *PLoS ONE* 2011, 6, e22182.
(2) Fells, J. I.; Lee, S. C.; Norman, D. D.; Tsukahara, R.; Kirby, J. R.; Nelson, S.; Seibel, W.; Papoian, R.; Patil, R.; Miller, D. D.; Parrill, A. L.; Pham, T.-C.; Baker, D. L.; Bittman, R.; Tigyi, G. *FEBS Journal* 2014, 281, 1017.
(3) Albers, H. M. H. G.; van Meeteren, L. A.; Egan, D. A.; van Tilburg, E. W.; Moolenaar, W. H.; Ovaa, H. *Journal of Medicinal Chemistry* 2010, 53, 4958.
(4) Albers, H. M. H. G.; Ovaa, H. *Chemical Reviews* 2012, 112, 2593.
(5) Fells, J. I.; Lee, S. C.; Fujiwara, Y.; Norman, D. D.; Lim, K. G.; Tsukahara, R.; Liu, J.; Patil, R.; Miller, D. D.; Kirby, R. J.; Nelson, S.; Seibel, W.; Papoian, R.; Parrill, A. L.; Baker, D. L.; Bittman, R.; Tigyi, G. *Molecular Pharmacology* 2013, 84, 415.
(6) Hoeglund, A. B.; Bostic, H. E.; Howard, A. L.; Wanjala, I. W.; Best, M. D.; Baker, D. L.; Parrill, A. L. *Journal of Medicinal Chemistry* 2010, 53, 1056.
(7) Castagna, D.; Budd, D. C.; Macdonald, S. J. F.; Jamieson, C.; Watson, A. J. B. *Journal of Medicinal Chemistry* 2016.
(8) Gupte, R.; Patil, R.; Liu, J.; Wang, Y.; Lee, S. C.; Fujiwara, Y.; Fells, J.; Bolen, A. L.; Emmons-Thompson, K.; Yates, C. R.; Siddam, A.; Panupinthu, N.; Pham, T.-C. T.; Baker, D. L.; Parrill, A. L.; Mills, G. B.; Tigyi, G.; Miller, D. D. *Chem Med Chem* 2011, 6, 922.
(9) Sue-Chin., L.; Yuko., F.;., L. J.; Junming., Y.; Yaohong., W.; Ryoko., T.; Erzsebet., S.; Renukadevi., P.; Souvik., B.; Duane., M. D.; ., B. L.; ., G. C. M.; Christopher., W. M.; Tamas., O.; Tigyi, G. J. *Molecular Cancer Research* 2014.
(10) Barbayianni, E.; Kaffe, E.; Aidinis, V.; Kokotos, G. *Progress in Lipid Research* 2015, 58, 76.
(11) Gotoh, M.; Fujiwara, Y.; Yue, J.; Liu, J.; Lee, S.; Fells, J.; Uchiyama, A.; Murakami-Murofushi, K.; Kennel, S.; Wall, J.; Patil, R.; Gupte, R.; Balazs, L.; Miller, Duane D.; Tigyi, Gabor J. *Biochemical Society Transactions* 2012, 40, 31.
(12) Castagna, D.; Duffy, E. L.; Semaan, D.; Young, L. C.; Pritchard, J. M.; Macdonald, S. J. F.; Budd, D. C.; Jamieson, C.; Watson, A. J. B. *Med Chem Comm* 2015, 6, 1149.
(13) Norman, D. D.; Ibezim, A.; Scott, W. E.; White, S.; Parrill, A. L.; Baker, D. L. *Bioorganic & Medicinal Chemistry* 2013, 21, 5548.
(14) Mize, C. D.; Abbott, A. M.; Gacasan, S. B.; Parrill, A. L.; Baker, D. L. *Journal of Molecular Graphics and Modelling* 2011, 31, 76.
(15) Barbayianni, E.; Magrioti, V.; Moutevelis-Minakakis, P.; Kokotos, G. *Expert Opinion on Therapeutic Patents* 2013, 23, 1123.
(16) Sotirios, K.; Eleftherios, B.; Dimitra, H.-L. *Current Medicinal Chemistry* 2015, 22, 1428.
(17) Saga, H.; Ohhata, A.; Hayashi, A.; Katoh, M.; Maeda, T.; Mizuno, H.; Takada, Y.; Komichi, Y.; Ota, H.; Matsumura, N.; Shibaya, M.; Sugiyama, T.; Nakade, S.; Kishikawa, K. *PLoS ONE* 2014, 9, e93230.
(18) Albers, H. M. H. G.; Hendrickx, L. J. D.; van Tol, R. J. P.; Hausmann, J.; Perrakis, A.; Ovaa, H. *Journal of Medicinal Chemistry* 2011, 54, 4619.
(19) Hausmann, J.; Kamtekar, S.; Christodoulou, E.; Day, J. E.; Wu, T.; Fulkerson, Z.; Albers, H. M. H. G.; van Meeteren, L. A.; Houben, A. J. S.; van Zeijl, L.; Jansen, S.; Andries, M.; Hall, T.; Pegg, L. E.; Benson, T. E.; Kasiem, M.; Harlos, K.; Kooi, C. W. V.; Smyth, S. S.; Ovaa, H.; Bollen, M.; Morris, A. J.; Moolenaar, W. H.; Perrakis, A. *Nat Struct Mol Biol* 2011, 18, 198.
(20) Nishimasu, H.; Okudaira, S.; Hama, K.; Mihara, E.; Dohmae, N.; Inoue, A.; Ishitani, R.; Takagi, J.; Aoki, J.; Nureki, O. *Nat StructMol Biol* 2011, 18, 205.
(21) Stein, A. J.; Bain, G.; Prodanovich, P.; Santini, A. M.; Darlington, J.; Stelzer, N. M. P.; Sidhu, R. S.; Schaub, J.; Goulet, L.; Lonergan, D.; Calderon, I.; Evans, J. F.; Hutchinson, J. H. *Molecular Pharmacology* 2015, 88, 982.
(22) Banerjee, S.; Smith, J.; Smith, J.; Faulkner, C.; Masterson, D. S. *J. Org. Chem.* 2012, 77, 10925.
(23) Pelcman, B.; Olofsson, K.; Suna, E.; Kalvins, I.; Ozola, V.; Andrianov, V.; Google Patents: 2008.
(24) Rashad, A. A.; Jones, A. J.; Avery, V. M.; Baell, J.; Keller, P. A. *ACS Medicinal Chemistry Letters* 2014, 5, 496.
(25) Cholody, W. M.; Zang, Y.; Zuck, K.; Watthey, J. W. H.; Ohler, Z.; Strovel, J.; Ohler, N. E.; Chellappan, S.; Padia, J.; Google Patents: 2010.
(26) Alyar, S.; Özbek, N.; Kuzukiran, K.; Karacan, N. *Med Chem Res* 2010, 20, 175.
(27) Cacchi, S.; Fabrizi, G.; Goggiamani, A.; Licandro, E.; Maiorana, S.; Perdicchia, D. *Organic Letters* 2005, 7, 1497.
(28) De Luca, L.; Giacomelli, G. *The Journal of Organic Chemistry* 2008, 73, 3967.
(29) Kim, J.-G.; Jang, D. O. *Synlett* 2007, 2007, 2501.
(30) Rosen, B. R.; Ruble, J. C.; Beauchamp, T. J.; Navarro, A. *Organic Letters* 2011, 13, 2564.
(31) Gupte, R.; Patil, R.; Liu, J.; Wang, Y.; Lee, S. C.; Fujiwara, Y.; Fells, J.; Bolen, A. L.; Emmons-Thompson, K.; Yates, C. R.; Siddam, A.; Panupinthu, N.; Pham, T. C.; Baker, D. L.; Parrill, A. L.; Mills, G. B.; Tigyi, G.; Miller, D. D. *Chem Med Chem* 2011, 6, 922.
(32) Hrast, M.; Turk, S.; Sosič, I.; Knez, D.; Randall, C. P.; Barreteau, H.; Contreras-Martel, C.; Dessen, A.; O'Neill, A. J.; Mengin-Lecreulx, D.; Blanot, D.; Gobec, S. *European Journal of Medicinal Chemistry* 2013, 66, 32.
(33) Leahy, J. W.; Buhr, C. A.; Johnson, H. W. B.; Kim, B. G.; Baik, T.; Cannoy, J.; Forsyth, T. P.; Jeong, J. W.; Lee, M. S.; Ma, S.; Noson, K.; Wang, L.; Williams, M.; Nuss, J. M.; Brooks, E.; Foster, P.; Goon, L.; Heald, N.; Holst, C.; Jaeger, C.; Lam, S.; Lougheed, J.; Nguyen, L.; Plonowski, A.; Song, J.; Stout, T.; Wu, X.; Yakes, M. F.; Yu, P.; Zhang, W.; Lamb, P.; Raeber, O. *Journal of Medicinal Chemistry* 2012, 55, 5467.
(34) Fischer, D. J.; Nusser, N.; Virag, T.; Yokoyama, K.; Wang, D.-a.; Baker, D. L.; Bautista, D.; Parrill, A. L.; Tigyi, G. *Molecular Pharmacology* 2001, 60, 776.
(35) Lin, F.-T.; Lai, Y.-J.; Makarova, N.; Tigyi, G.; Lin, W.-C. *Journal of Biological Chemistry* 2007, 282, 37759.

(36) Kiss, G. N.; Fells, J. I.; Gupte, R.; Lee, S.-C.; Liu, J.; Nusser, N.; Lim, K. G.; Ray, R. M.; Lin, F.-T.; Parrill, A. L.; Sumegi, B.; Miller, D. D.; Tigyi, G. *Molecular Pharmacology* 2012, 82, 1162.
The invention claimed is:
1. A compound having the structure:
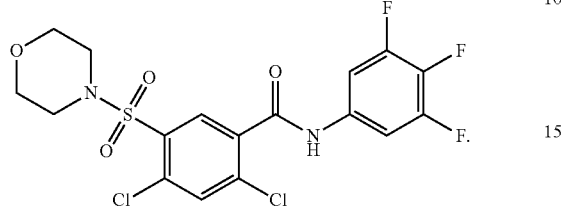
SB1-85 (3b)
* * * * *